United States Patent
Laurie

(10) Patent No.: US 10,302,658 B2
(45) Date of Patent: May 28, 2019

(54) COMPOSITIONS AND METHODS FOR TREATING EYE INFECTIONS AND DISEASE

(71) Applicant: UNIVERSITY OF VIRGINIA PATENT FOUNDATION, Charlottesville, VA (US)

(72) Inventor: Gordon W. Laurie, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 0 days.

(21) Appl. No.: 15/125,357

(22) PCT Filed: Mar. 11, 2015

(86) PCT No.: PCT/US2015/019964
§ 371 (c)(1),
(2) Date: Sep. 12, 2016

(87) PCT Pub. No.: WO2015/138604
PCT Pub. Date: Sep. 17, 2015

(65) Prior Publication Data
US 2017/0176457 A1    Jun. 22, 2017

Related U.S. Application Data

(60) Provisional application No. 61/951,680, filed on Mar. 12, 2014, provisional application No. 62/019,476, filed on Jul. 1, 2014.

(51) Int. Cl.
| | |
|---|---|
| *G01N 33/68* | (2006.01) |
| *A61K 38/18* | (2006.01) |
| *C07K 14/475* | (2006.01) |
| *G01N 33/573* | (2006.01) |
| *A61K 9/00* | (2006.01) |
| *A61K 38/17* | (2006.01) |

(52) U.S. Cl.
CPC ....... *G01N 33/6893* (2013.01); *A61K 9/0048* (2013.01); *A61K 38/1709* (2013.01); *A61K 38/18* (2013.01); *C07K 14/475* (2013.01); *C12Y 302/01166* (2013.01); *G01N 33/573* (2013.01); *G01N 33/68* (2013.01); *G01N 2333/4706* (2013.01); *G01N 2333/4722* (2013.01); *G01N 2333/4728* (2013.01); *G01N 2333/70596* (2013.01); *G01N 2333/924* (2013.01); *G01N 2800/16* (2013.01); *G01N 2800/162* (2013.01)

(58) Field of Classification Search
None
See application file for complete search history.

(56) References Cited

U.S. PATENT DOCUMENTS

| | | | |
|---|---|---|---|
| 7,320,870 B2 | 1/2008 | Laurie et al. | |
| 7,459,440 B2 | 12/2008 | Laurie et al. | |
| 2007/0167372 A1 | 7/2007 | Laurie et al. | |
| 2007/0207522 A1* | 9/2007 | Laurie | C07K 14/475 435/69.1 |
| 2011/0065189 A1* | 3/2011 | Laurie | A61K 38/47 435/375 |
| 2011/0124572 A1* | 5/2011 | Szilak | C07K 14/4725 514/17.6 |
| 2017/0176457 A1* | 6/2017 | Laurie | G01N 33/573 |

FOREIGN PATENT DOCUMENTS

| | | |
|---|---|---|
| WO | WO1998/27205 | 6/1998 |
| WO | WO1998/35299 | 8/1998 |
| WO | WO2002/065943 | 8/2002 |
| WO | WO2004/037167 | 6/2004 |
| WO | WO2005/119899 | 12/2005 |
| WO | WO 2005119899 | * 12/2005 |
| WO | WO 2011/034207 | 3/2011 |

OTHER PUBLICATIONS

Zhang et al., "Targeting of Heparanase-modified Syndecan-1 by Prosecretory Mitogen Lacritin Requires Conserved Core GAGAL plus Heparan and Chondroitin Sulfate as a Novel Hybrid Binding Site That Enhances Selectivity," 2013, Journal of Biological Chemistry, vol. 288, Nr:17, pp. 12090-12101.*
Ma et al. Heparanase deglycanation of syndecan-1 is required for binding of the epithelial-restricted prosecretory mitogen lacritin. J Cell Biol. Sep. 25, 2006. vol. 174. No. 7. pp. 1097-1106.*
Karnati et al., "Lacritin and the Tear Proteome as Natural Replacement Therapy for Dry Eye", Experimental Eye Research, vol. 117, p. 39-52, Jun. 12, 2013.
Zhang et al., "Focus on Molecules: Syndecan-1," Experimental Eye Research, vol. 93, No. 4, p. 329-330, Jun. 23, 2010.
PCT Search Report and Written Opinion for PCT/US2015/019964, completed Jul. 8, 2015.
Zhang, Y., et al., "Targeting of Heparanase-modified Syndecan-1 by Prosecretory Mitogen Lacritin Requires conserved Core GAGAL plus Heparan and Chondroitin Sulfate as a Novel Hybrid Binding Site That Enhances Selectivity," 2013, Journal of Biological Chemistry, vol. 288, Nr:17, pp. 12090-12101.
Peisong, Ma, et al., "Heparanase Deglycanation of Syndecan-1 is Required for Binding of the Epithelial-Restricted Prosecretory Mitogen Lacritina," 2006, The journal of cell biology, vol. 174, Nr:7, pp. 1097-1106.

(Continued)

*Primary Examiner* — Maury A Audet
(74) *Attorney, Agent, or Firm* — Knobbe, Martens, Olson & Bear, LLP

(57) ABSTRACT

The present invention provides compositions and methods for identifying subjects suffering from dry eye that can be treated by topical administration of a composition comprising lacritin or a bioactive fragment thereof. The application discloses in part that a ~90 KDa deglycanated form of syndecan-1 is abundant in tears of normal individuals but not individuals suffering from dry eye, whereas a ~25 kDa syndecan-1 fragment is detectable in dry, but no normal tears.

8 Claims, 12 Drawing Sheets
Specification includes a Sequence Listing.

(56) References Cited

OTHER PUBLICATIONS

McKown, R. L., et al., "Lacritin and Other New Proteins of the Lacrimal Functional Unit," 2009, Experimental Eye Research, vol. 88, Nr:5, pp. 848-858.

Boehm, Nils, et al., "Alterations in the Tear Proteome of Dry Eye Patients—A Matter of the Clinical Phenotype," 2013, Investigative Opthalmology & Visual Science, vol. 54, Nr:3, pp. 2385.

Zimmermann P., et al., "The Syndecans, Tuners of Transmembrane Signalling," 1999, The FASEB Journal, vol. 13 (Suppl.), pp. S91-S100.

Still et al., "Development of Quantitative Sandwich ELISAs for Lacritin and the Lacritin-c Splice Variant in Human Tears", IOVS Meeting Abstract, Mar. 2012, vol. 53, No. 14.

Laurie et al., "Restricted epithelial proliferation by lacritin via PKCa-dependent NFAT and mTOR pathways," JCB, Aug. 2006, vol. 174, No. 5 pp. 689-700.

McKown et al., "A Cleavage-Potentiated Fragment of Tear Lacritin Is Bactericidal," JBC, vol. 289, No. 32, Aug. 8, 2014, pp. 22172-22182.

\* cited by examiner

```
Human:        K Q F I E N G S E F A Q K L L K K F S L L K P W A
Chimpanzee:   K Q F I E N G S E F A Q K L L K K F S L L K P W A
Bushbaby:     K Q L V E G G S D F L Q Q M M K K L H P L K F W F S
Gorilla:      K Q F I E N G S E V A Q K L L K K F S L L K P W A
Macaque:      K Q F I E N G N E F A K K L L K K F G L P K P W A
Marmoset:     K Q F F E S R N E A A Q K L L K R F G L T K L W N
Mouse Lemur   K K L V G D G N D F V Q Q L M K K W H P L K M W F
Orangutan:    K Q F I E N G S E F A Q K L L K K F S L L K P W A
```

Fig. 9

SEQUENCE LISTING

<160> NUMBER OF SEQ ID NOS: 28

<210> SEQ ID NO 1
<211> LENGTH: 138

```
<212> TYPE: PRT
<213> ORGANISM: Homo sapiens

<400> SEQUENCE: 1

Met Lys Phe Thr Thr Leu Leu Phe Leu Ala Ala Val Ala Gly Ala Leu
1               5                   10                  15

Val Tyr Ala Glu Asp Ala Ser Ser Asp Ser Thr Gly Ala Asp Pro Ala
            20                  25                  30

Gln Glu Ala Gly Thr Ser Lys Pro Asn Glu Glu Ile Ser Gly Pro Ala
        35                  40                  45

Glu Pro Ala Ser Pro Pro Glu Thr Thr Thr Thr Ala Gln Glu Thr Ser
50                  55                  60

Ala Ala Ala Val Gln Gly Thr Ala Lys Val Thr Ser Ser Arg Gln Glu
65                  70                  75                  80

Leu Asn Pro Leu Lys Ser Ile Val Glu Lys Ser Ile Leu Leu Thr Glu
                85                  90                  95

Gln Ala Leu Ala Lys Ala Gly Lys Gly Met His Gly Gly Val Pro Gly
            100                 105                 110

Gly Lys Gln Phe Ile Glu Asn Gly Ser Glu Phe Ala Gln Lys Leu Leu
        115                 120                 125

Lys Lys Phe Ser Leu Leu Lys Pro Trp Ala
130                 135

<210> SEQ ID NO 2
<211> LENGTH: 310
<212> TYPE: PRT
<213> ORGANISM: Homo sapiens

<400> SEQUENCE: 2

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205
```

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
                275                 280                 285

Glu Glu Pro Lys Gln Ala Asn Gly Gly Ala Tyr Gln Lys Pro Thr Lys
290                 295                 300

Gln Glu Glu Phe Tyr Ala
305                 310

<210> SEQ ID NO 3
<211> LENGTH: 229
<212> TYPE: PRT
<213> ORGANISM: Homo sapiens

<400> SEQUENCE: 3

Gln Ile Val Ala Thr Asn Leu Pro Pro Glu Asp Gln Asp Gly Ser Gly
1               5                   10                  15

Asp Asp Ser Asp Asn Phe Ser Gly Ser Gly Ala Gly Ala Leu Gln Asp
                20                  25                  30

Ile Thr Leu Ser Gln Gln Thr Pro Ser Thr Trp Lys Asp Thr Gln Leu
            35                  40                  45

Leu Thr Ala Ile Pro Thr Ser Pro Glu Pro Thr Gly Leu Glu Ala Thr
50                  55                  60

Ala Ala Ser Thr Ser Thr Leu Pro Ala Gly Glu Gly Pro Lys Glu Gly
65                  70                  75                  80

Glu Ala Val Val Leu Pro Glu Val Glu Pro Gly Leu Thr Ala Arg Glu
                85                  90                  95

Gln Glu Ala Thr Pro Arg Pro Arg Glu Thr Thr Gln Leu Pro Thr Thr
            100                 105                 110

His Gln Ala Ser Thr Thr Thr Ala Thr Thr Ala Gln Glu Pro Ala Thr
        115                 120                 125

Ser His Pro His Arg Asp Met Gln Pro Gly His His Glu Thr Ser Thr
    130                 135                 140

Pro Ala Gly Pro Ser Gln Ala Asp Leu His Thr Pro His Thr Glu Asp
145                 150                 155                 160

Gly Gly Pro Ser Ala Thr Glu Arg Ala Ala Glu Asp Gly Ala Ser Ser
                165                 170                 175

Gln Leu Pro Ala Ala Glu Gly Ser Gly Glu Gln Asp Phe Thr Phe Glu
            180                 185                 190

Thr Ser Gly Glu Asn Thr Ala Val Val Ala Val Glu Pro Asp Arg Arg
        195                 200                 205

Asn Gln Ser Pro Val Asp Gln Gly Ala Thr Gly Ala Ser Gln Gly Leu
    210                 215                 220

Leu Asp Arg Lys Glu
225

<210> SEQ ID NO 4
<211> LENGTH: 543
<212> TYPE: PRT
<213> ORGANISM: Homo sapiens

<400> SEQUENCE: 4

Met Leu Leu Arg Ser Lys Pro Ala Leu Pro Pro Leu Met Leu Leu
1               5                   10                  15

Leu Leu Gly Pro Leu Gly Pro Leu Ser Pro Gly Ala Leu Pro Arg Pro
            20                  25                  30

Ala Gln Ala Gln Asp Val Val Asp Leu Asp Phe Phe Thr Gln Glu Pro
            35                  40                  45

Leu His Leu Val Ser Pro Ser Phe Leu Ser Val Thr Ile Asp Ala Asn
        50                  55                  60

Leu Ala Thr Asp Pro Arg Phe Leu Ile Leu Leu Gly Ser Pro Lys Leu
65                  70                  75                  80

Arg Thr Leu Ala Arg Gly Leu Ser Pro Ala Tyr Leu Arg Phe Gly Gly
                85                  90                  95

Thr Lys Thr Asp Phe Leu Ile Phe Asp Pro Lys Lys Glu Ser Thr Phe
                    100                 105                 110

Glu Glu Arg Ser Tyr Trp Gln Ser Gln Val Asn Gln Asp Ile Cys Lys
                115                 120                 125

Tyr Gly Ser Ile Pro Pro Asp Val Glu Glu Lys Leu Arg Leu Glu Trp
130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                165                 170                 175

Ala Asn Cys Ser Gly Leu Asp Leu Ile Phe Gly Leu Asn Ala Leu Leu
                180                 185                 190

Arg Thr Ala Asp Leu Gln Trp Asn Ser Ser Asn Ala Gln Leu Leu Leu
                195                 200                 205

Asp Tyr Cys Ser Ser Lys Gly Tyr Asn Ile Ser Trp Glu Leu Gly Asn
210                 215                 220

Glu Pro Asn Ser Phe Leu Lys Lys Ala Asp Ile Phe Ile Asn Gly Ser
225                 230                 235                 240

Gln Leu Gly Glu Asp Phe Ile Gln Leu His Lys Leu Leu Arg Lys Ser
                245                 250                 255

Thr Phe Lys Asn Ala Lys Leu Tyr Gly Pro Asp Val Gly Gln Pro Arg
                260                 265                 270

Arg Lys Thr Ala Lys Met Leu Lys Ser Phe Leu Lys Ala Gly Gly Glu
                275                 280                 285

Val Ile Asp Ser Val Thr Trp His His Tyr Tyr Leu Asn Gly Arg Thr
290                 295                 300

Ala Thr Lys Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
                325                 330                 335

Lys Lys Val Trp Leu Gly Glu Thr Ser Ser Ala Tyr Gly Gly Gly Ala
                340                 345                 350

Pro Leu Leu Ser Asp Thr Phe Ala Ala Gly Phe Met Trp Leu Asp Lys
                355                 360                 365

Leu Gly Leu Ser Ala Arg Met Gly Ile Glu Val Val Met Arg Gln Val
                370                 375                 380

Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Lys Leu Val Gly Thr

```
                        405                 410                 415
Lys Val Leu Met Ala Ser Val Gln Gly Ser Lys Arg Arg Lys Leu Arg
            420                 425                 430

Val Tyr Leu His Cys Thr Asn Thr Asp Asn Pro Arg Tyr Lys Glu Gly
        435                 440                 445

Asp Leu Thr Leu Tyr Ala Ile Asn Leu His Asn Val Thr Lys Tyr Leu
    450                 455                 460

Arg Leu Pro Tyr Pro Phe Ser Asn Lys Gln Val Asp Lys Tyr Leu Leu
465                 470                 475                 480

Arg Pro Leu Gly Pro His Gly Leu Leu Ser Lys Ser Val Gln Leu Asn
                485                 490                 495

Gly Leu Thr Leu Lys Met Val Asp Asp Gln Thr Leu Pro Pro Leu Met
            500                 505                 510

Glu Lys Pro Leu Arg Pro Gly Ser Ser Leu Gly Leu Pro Ala Phe Ser
        515                 520                 525

Tyr Ser Phe Phe Val Ile Arg Asn Ala Lys Val Ala Ala Cys Ile
    530                 535                 540

<210> SEQ ID NO 5
<211> LENGTH: 19
<212> TYPE: PRT
<213> ORGANISM: Homo sapiens

<400> SEQUENCE: 5

Lys Gln Phe Ile Glu Asn Gly Ser Glu Phe Ala Gln Lys Leu Leu Lys
1               5                   10                  15

Lys Phe Ser

<210> SEQ ID NO 6
<211> LENGTH: 19
<212> TYPE: PRT
<213> ORGANISM: Homo sapiens

<400> SEQUENCE: 6

Lys Gln Phe Ile Glu Asn Gly Ser Glu Phe Ala Asn Lys Leu Leu Lys
1               5                   10                  15

Lys Phe Ser

<210> SEQ ID NO 7
<211> LENGTH: 25
<212> TYPE: PRT
<213> ORGANISM: Homo sapiens

<400> SEQUENCE: 7

Lys Gln Phe Ile Glu Asn Gly Ser Glu Phe Ala Gln Lys Leu Leu Lys
1               5                   10                  15

Lys Phe Ser Leu Leu Lys Pro Trp Ala
            20                  25

<210> SEQ ID NO 8
<211> LENGTH: 25
<212> TYPE: PRT
<213> ORGANISM: Homo sapiens

<400> SEQUENCE: 8

Lys Gln Phe Ile Glu Asn Gly Ser Glu Phe Ala Asn Lys Leu Leu Lys
1               5                   10                  15

Lys Phe Ser Leu Leu Lys Pro Trp Ala
            20                  25
```

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
ggtggtcata tgaaagcagg aaaaggaatg cacgg                     35

<210> SEQ ID NO 10
<211> LENGTH: 35
<212> TYPE: DNA
<213> ORGANISM: Artificial Sequence
<220> FEATURE:
<223> OTHER INFORMATION: Primer

<400> SEQUENCE: 10
ggtggtcata tgaaagcagg aaaaggaatg cacgg                     35

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
ggtggtcata tgtatatctc cttcttaaag                           30

<210> SEQ ID NO 12
<211> LENGTH: 7
<212> TYPE: PRT
<213> ORGANISM: Homo sapiens

<400> SEQUENCE: 12

Leu Ala Lys Ala Gly Lys Gly
1               5

<210> SEQ ID NO 13
<211> LENGTH: 14
<212> TYPE: PRT
<213> ORGANISM: Homo sapiens

<400> SEQUENCE: 13

Ala Lys Ala Gly Lys Gly Met His Gly Gly Val Pro Gly Gly
1               5                   10

<210> SEQ ID NO 14
<211> LENGTH: 24
<212> TYPE: PRT
<213> ORGANISM: Homo sapiens

<400> SEQUENCE: 14

Leu Lys Ser Ile Val Glu Lys Ser Ile Leu Leu Thr Glu Gln Ala Leu
1               5                   10                  15

Ala Lys Ala Gly Lys Gly Met His
            20

<210> SEQ ID NO 15
<211> LENGTH: 21
<212> TYPE: PRT
<213> ORGANISM: Homo sapiens

```
<400> SEQUENCE: 15

Glu Asn Gly Ser Glu Phe Ala Gln Lys Leu Leu Lys Lys Phe Ser Leu
1               5                   10                  15

Leu Lys Pro Trp Ala
            20

<210> SEQ ID NO 16
<211> LENGTH: 16
<212> TYPE: PRT
<213> ORGANISM: Homo sapiens

<400> SEQUENCE: 16

Phe Ala Gln Lys Leu Leu Lys Lys Phe Ser Leu Leu Lys Pro Trp Ala
1               5                   10                  15

<210> SEQ ID NO 17
<211> LENGTH: 25
<212> TYPE: PRT
<213> ORGANISM: Pan troglodytes

<400> SEQUENCE: 17

Lys Gln Phe Ile Glu Asn Gly Ser Glu Phe Ala Gln Lys Leu Leu Lys
1               5                   10                  15

Lys Phe Ser Leu Leu Lys Pro Trp Ala
            20                  25

<210> SEQ ID NO 18
<211> LENGTH: 26
<212> TYPE: PRT
<213> ORGANISM: Otolemur crassicaudatus

<400> SEQUENCE: 18

Lys Gln Leu Val Glu Gly Gly Ser Asp Phe Leu Gln Gln Met Met Lys
1               5                   10                  15

Lys Leu His Pro Leu Lys Phe Trp Phe Ser
            20                  25

<210> SEQ ID NO 19
<211> LENGTH: 25
<212> TYPE: PRT
<213> ORGANISM: Gorilla gorilla

<400> SEQUENCE: 19

Lys Gln Phe Ile Glu Asn Gly Ser Glu Val Ala Gln Lys Leu Leu Lys
1               5                   10                  15

Lys Phe Ser Leu Leu Lys Pro Trp Ala
            20                  25

<210> SEQ ID NO 20
<211> LENGTH: 25
<212> TYPE: PRT
<213> ORGANISM: Macaca arctoides

<400> SEQUENCE: 20

Lys Gln Phe Ile Glu Asn Gly Asn Glu Phe Ala Lys Lys Leu Leu Lys
1               5                   10                  15

Lys Phe Gly Leu Pro Lys Pro Trp Ala
            20                  25

<210> SEQ ID NO 21
<211> LENGTH: 25
<212> TYPE: PRT
```

```
<213> ORGANISM: Callithrix jacchus

<400> SEQUENCE: 21

Lys Gln Phe Phe Glu Ser Arg Asn Glu Ala Ala Gln Lys Leu Leu Lys
1               5                   10                  15

Arg Phe Gly Leu Thr Lys Leu Trp Asn
            20                  25

<210> SEQ ID NO 22
<211> LENGTH: 25
<212> TYPE: PRT
<213> ORGANISM: Microcebus coquereli

<400> SEQUENCE: 22

Lys Lys Leu Val Gly Asp Gly Asn Asp Phe Val Gln Gln Leu Met Lys
1               5                   10                  15

Lys Trp His Pro Leu Lys Met Trp Phe
            20                  25

<210> SEQ ID NO 23
<211> LENGTH: 25
<212> TYPE: PRT
<213> ORGANISM: Pongo pygmaeus

<400> SEQUENCE: 23

Lys Gln Phe Ile Glu Asn Gly Ser Glu Phe Ala Gln Lys Leu Leu Lys
1               5                   10                  15

Lys Phe Ser Leu Leu Lys Pro Trp Ala
            20                  25

<210> SEQ ID NO 24
<211> LENGTH: 5
<212> TYPE: PRT
<213> ORGANISM: artificial sequence
<220> FEATURE:
<223> OTHER INFORMATION: elastin-like polypeptide
<220> FEATURE:
<221> NAME/KEY: MISC_FEATURE
<222> LOCATION: (4)..(4)
<223> OTHER INFORMATION: Xaa at position 4 is serine or isoleucine

<400> SEQUENCE: 24

Val Pro Gly Xaa Gly
1               5

<210> SEQ ID NO 25
<211> LENGTH: 406
<212> TYPE: DNA
<213> ORGANISM: Artificial Sequence
<220> FEATURE:
<223> OTHER INFORMATION: synthetic lacritin with restriction sties added

<400> SEQUENCE: 25
catatggaag acgcttcttc tgactctacc ggtgctgacc cggctcagga agctggtacc      60
tctaaaccga acgaagaaat ctctggtccg gctgaaccgg cttctccgcc ggaaaccacc     120
accaccgctc aggaaacctc tgctgctgct gttcagggta ccgctaaagt tacctcttct     180
cgtcaggaac tgaacccgct gaaatctatc gttgaaaaat ctatcctgct gaccgaacag     240
gctctggcta aagctggtaa aggtatgcac ggtggtgttc gggtggtaa acagttcatc      300 gaaaacggtt ctgaattcgc tcagaaactg ctgaaaaaat ctctctctgct gaaaccgtgg    360 gctggtctgg ttccgcgtgg ttctggttac tgatctcctc ggatcc                    406
```

```
<210> SEQ ID NO 26
<211> LENGTH: 139
<212> TYPE: PRT
<213> ORGANISM: Artificial Sequence
<220> FEATURE:
<223> OTHER INFORMATION: ELP lacritin fusion construct
<220> FEATURE:
<221> NAME/KEY: MISC_FEATURE
<222> LOCATION: (129)..(133)
<223> OTHER INFORMATION: the sequence VPGSG is directly repeated 48
      times
<220> FEATURE:
<221> NAME/KEY: MISC_FEATURE
<222> LOCATION: (134)..(138)
<223> OTHER INFORMATION: The sequence VPGIG is directly repeated 48
      times

<400> SEQUENCE: 26

Gly Glu Asp Ala Ser Ser Asp Ser Thr Gly Ala Asp Pro Ala Gln Glu
1               5                   10                  15

Ala Gly Thr Ser Lys Pro Asn Glu Glu Ile Ser Gly Pro Ala Glu Pro
            20                  25                  30

Ala Ser Pro Pro Glu Thr Thr Thr Thr Ala Gln Glu Thr Ser Ala Ala
        35                  40                  45

Ala Val Gln Gly Thr Ala Lys Val Thr Ser Ser Arg Gln Glu Leu Asn
    50                  55                  60

Pro Leu Lys Ser Ile Val Glu Lys Ser Ile Leu Leu Thr Glu Gln Ala
65                  70                  75                  80

Leu Ala Lys Ala Gly Lys Gly Met His Gly Gly Val Pro Gly Gly Lys
                85                  90                  95

Gln Phe Ile Glu Asn Gly Ser Glu Phe Ala Gln Lys Leu Leu Lys Lys
            100                 105                 110

Phe Ser Leu Leu Lys Pro Trp Ala Gly Leu Val Pro Arg Gly Ser Gly
        115                 120                 125

Val Pro Gly Ser Gly Val Pro Gly Ile Gly Tyr
    130                 135

<210> SEQ ID NO 27
<211> LENGTH: 134
<212> TYPE: PRT
<213> ORGANISM: Artificial Sequence
<220> FEATURE:
<223> OTHER INFORMATION: ELP lacritin fusion construct
<220> FEATURE:
<221> NAME/KEY: MISC_FEATURE
<222> LOCATION: (129)..(133)
<223> OTHER INFORMATION: the sequence VPGSG is directly repeated 96
      times

<400> SEQUENCE: 27

Gly Glu Asp Ala Ser Ser Asp Ser Thr Gly Ala Asp Pro Ala Gln Glu
1               5                   10                  15

Ala Gly Thr Ser Lys Pro Asn Glu Glu Ile Ser Gly Pro Ala Glu Pro
            20                  25                  30

Ala Ser Pro Pro Glu Thr Thr Thr Thr Ala Gln Glu Thr Ser Ala Ala
        35                  40                  45

Ala Val Gln Gly Thr Ala Lys Val Thr Ser Ser Arg Gln Glu Leu Asn
    50                  55                  60

Pro Leu Lys Ser Ile Val Glu Lys Ser Ile Leu Leu Thr Glu Gln Ala
65                  70                  75                  80

Leu Ala Lys Ala Gly Lys Gly Met His Gly Gly Val Pro Gly Gly Lys
                85                  90                  95
```

```
Gln Phe Ile Glu Asn Gly Ser Glu Phe Ala Gln Lys Leu Leu Lys Lys
                100                 105                 110
Phe Ser Leu Leu Lys Pro Trp Ala Gly Leu Val Pro Arg Gly Ser Gly
            115                 120                 125
Val Pro Gly Ser Gly Tyr
        130

<210> SEQ ID NO 28
<211> LENGTH: 10
<212> TYPE: PRT
<213> ORGANISM: Artificial Sequence
<220> FEATURE:
<223> OTHER INFORMATION: ELP lacritin fusion construct
<220> FEATURE:
<221> NAME/KEY: MISC_FEATURE
<222> LOCATION: (1)..(5)
<223> OTHER INFORMATION: the sequence VPGSG is directly repeated 48
      times
<220> FEATURE:
<221> NAME/KEY: MISC_FEATURE
<222> LOCATION: (6)..(10)
<223> OTHER INFORMATION: The sequence VPGIG is directly repeated 48
      times

<400> SEQUENCE: 28

Val Pro Gly Ser Gly Val Pro Gly Ile Gly
1               5                   10
```

COMPOSITIONS AND METHODS FOR TREATING EYE INFECTIONS AND DISEASE

CROSS REFERENCE TO RELATED APPLICATIONS

This application is a national stage entry under 35 USC § 371(b) of PCT/US2015/019964, filed on Mar. 11, 2015, which claims priority to U.S. Provisional Application Nos. 61/951,680 filed on Mar. 12, 2014 and 62/019,476 filed on Jul. 1, 2014, the disclosures of which are hereby expressly incorporated by reference in their entirety, respectively.

STATEMENT REGARDING FEDERALLY SPONSORED RESEARCH OR DEVELOPMENT

This invention was made with government support under Grant Nos. RO1EY013143 and R01EY018222, awarded by The National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 19 kilobytes ACII (Text) file named "233965SeqListing.txt," created on Mar. 11, 2015.

BACKGROUND

Health of the ocular surface is dependent on tear fluid secretions from the lacrimal gland. The lacrimal acinar cells comprising the lacrimal gland are polarized and highly differentiated tear secreting cells that adhere to a complex periacinar basement membrane. The bulk of the apical cell cytoplasm contains large secretory granules packed with tear proteins. Known tear proteins include: lysozyme, which plays a prominent bactericidal role on the corneal surface; lactoferrin, which functions as both a bactericidal agent and as a potential inhibitor of complement activation; secretory component, which regulates the transcellular movement of IgA into acini lumen where it acts on the corneal surface to inhibit bacterial adhesion; and tear lipocalins (tear-specific prealbumin) and growth factors TGFα, TGFβ and EGF the functions of which are not known. In rats, peroxidase is a tear component which has served as a convenient marker in experimental studies. Tears not only have an important bactericidal role, they also keep the cornea clean and lubricated and are important for the well-being of the corneal epithelium.

The surface of the eye is one of the most accessible and vulnerable tissues. Corneal epithelial cells confront environmental insults constantly including: UV irradiation, widely varying air temperature fluxes, pollutants, bacteria and other microbial organisms. The tear fluid which bathes the corneal surface is the most likely source of cytoprotective and anti-inflammatory agents since the cornea lacks blood supply, unlike other tissues where blood vessels supply such agents. Indeed, tear fluid is rich in bactericidal proteins. Dry Eye subjects suffering insufficient tear production are subject to corneal ulceration, infection or inflammation. Similar symptoms can be generated by extended contact lens use, since volume of tear supply is limited.

When lacrimal acinar cell tear output is collectively deficient, 'Dry Eye' (also known as keratoconjunctivitis sicca [KCS]); is the result. Dry Eye is a common ocular manifestation of Sjogren's's syndrome, an autoimmune disease with unknown etiology that affects millions of people worldwide. Most commonly affected are post-menopausal women with varying degrees of severity. If untreated, Dry Eye can lead to corneal abrasion, ulceration, bacterial infection, and loss of vision. Molecular mechanisms underlying the pathogenic decline of secretory output by the main lacrimal gland are potentially multiple. Lacrimal glands of Sjogren's's syndrome subjects contain foci of B and T lymphocytes whose pathogenic expansion, possibly due to viral insult, can destroy lacrimal acini. However, acinar volume loss often appears insufficient relative to the theoretical overcapacity of the main lacrimal gland. Estimates suggest a potential secretory output up to ten-fold greater than is required to maintain a normal aqueous tear film layer. Other mechanisms therefore warrant attention, such as aberrant secretion of one or several common cytokines that may directly or indirectly alter lacrimal acinar cell function and/or lead to a decline in neural innervation. Novel autocrine/paracrine factor(s) released by lacrimal acinar cells into the tear film may be required for the health of the lacrimal secretory machinery, ductal system, and corneal epithelium. The periacinar basement membrane is also required for normal secretory function, in part via 'BM180' whose apparent synergy with laminin-1 promotes stimulated tear secretion. Alteration of each of these factors, together or independent of hormonal changes, could contribute to decreased secretory capacity.

The lacrimal-corneal axis is a fundamental regulator of ocular health and plays a key role in ocular surface inflammation associated with Dry Eye Syndromes and corneal injury. A host of mediators are implicated in the development and progression of corneal inflammation, such as the proinflammatory cytokines TNF-α, IL-1β, IL-6 and the chemokine IL-8. Also involved are the arachidonic acid-derived eicosanoids which are produced by the activity of cyclooxygenases (primarily PGE2), lipooxygenases (12 (s)-HETE) and cytochrome P450 (12 (r)-HETE).

Lacritin is a 12.3 kDa secreted glycoprotein that is apically released from human lacrimal acinar cells during reflex tearing and can be detected in mixed reflex and basal human tears by ELISA and Western blotting. Lacritin is also produced by corneal, conjunctival, meibomian, and salivary epithelia as one of the most eye-restricted genes. Recent studies on lacritin mechanisms of action indicate converging PKCα and NFkB signaling pathways suggesting that lacritin may have a key anti-inflammatory role on the ocular surface. Recent clinical studies support this hypothesis. Comparison of tear proteins from 19 subjects suffering from Blepharitis (inflammation of the lid) vs 27 healthy volunteers revealed lacritin to be decreased by 56% in subjects. Sumadre et al. (Invest Ophthalmol Vis Sci., 2011; 52:6265-6270; DOI: 10.1167/iovs.10-6220) showed that lacritin acutely increased basal tearing to 30% over vehicle and that multiple doses per day were well tolerated. It was also recently reported that lacritin is selectively downregulated more than any other tear protein in contact lens-related dry eye. Lacritin stimulates MUC16 production by human corneal epithelial cells at levels matching or exceeding that of serum (Laurie G E, et al. IOVS 2006; 47:ARVO E-Abstract 1606). Autologous serum is a reportedly successful method of treating dry eye. Lacritin also promotes basal tear secretion by cultured rat and monkey lacrimal acinar cells and stimulates human corneal epithelial cell growth.

Few cell types appear capable of being targeted by lacritin. Targeted cells include lacrimal acinar, salivary ductal/HeLa, human corneal, and embryonic kidney cells, but no others among 17 different cell lines tested. Its co-receptor syndecan-1 is widely expressed on ocular surface epithelia. Thus, lacritin appears to be a multifunctional eye-specific factor with a potential role in tear secretion and corneal epithelial renewal.

There is a long felt need in the art for compositions and methods useful for detecting and diagnosing dry eye, treating dry eye, and developing treatment strategies and regimens based on the a diagnosis of dry eye. The present invention satisfies these needs.

SUMMARY

The present invention couples a novel mechanism for the molecular identification of dry eye disease with a restorative therapy that addresses cause. The invention relates to the discovery disclosed herein that a ~90 KDa deglycanated form of syndecan-1 is abundant in tears of normal individuals but not in individuals suffering from dry eye. Furthermore a ~25 kDa syndecan-1 fragment is detectable in dry, but not normal tears. The invention also relates to the discovery that topical lacritin, the agonist of deglycanated syndecan-1, sensitizes corneal sensory nerves to drying of the surface of the eye, and increases the neural wet response. Accordingly, one embodiment of the present invention is directed to identifying dry eye by a relative decrease in ~90 kDa deglycanated form of syndecan-1 and/or the presence of 25 kDa syndecan-1 in tears. Another embodiment is directed to increasing the corneal neural dry and wet responses by topical application of a lacritin polypeptide to the eye.

Applicants have also discovered that that aqueous deficient dry eye tears are associated with decreased lacritin monomer, increased lacritin-C splice variant, and latent (chronically active) heparanase (HPSE). Accordingly, in one embodiment a method is provided for identifying patients suffering from dry eye and selecting such patient for treatment. In one embodiment a method for identifying a subject having dry eye is provided wherein the presence of at least one protein selected from the group consisting of
  latent heparanase;
  90 kDa deglycanated SDC-1;
  25 kDa SDC-1; and
  inactive lacritin-C splice variant;
is detected in a tear sample obtained from the subject. Patients with dry eye are then identified by those that have one or more of the following:
  a decreased level of latent heparanase and a corresponding increase in active heparanase, relative to levels present in tears from a normal eye;
  a decreased level of 90 kDa deglycanated SDC-1, relative to levels present in tears from a normal eye;
  presence of 25 kDa SDC-1; and/or
  presence of inactive lacritin-C splice variant. Such identified subjects can then be treated by contacting the ocular surface of the subject's eyes with a composition comprising lacritin or a bioactive fragment thereof.

The detection of latent heparanase, 90 kDa deglycanated SDC-1A, 25 kDa SDC-1 or inactive lacritin-C splice variant can be conducted using standard techniques known to those skilled in the art, including the use of antibodies. In one embodiment antibodies could be embedded in Schirmer strips on which tears are collected for precise and inexpensive molecular diagnosis in an ophthalmologist's or optometrist's office. Current approaches for identifying subjects afflicted with dry eye do not address cause, and therefore suffer from inaccuracy and are nonspecific. Examples of current methods include: a) subject questionnaires, b) rose bengal or lissamine green staining of ocular surface damage, c) Schirmer strip measurement of tear volume, d) tear break up time, e) tear evaporation rate, 0 tear meniscus height or radius, g) tear film index or turnover rate, h) tear osmolarity, i) lysozyme or lactoferrin assay, and j) tear ferning analysis.

Restoration of active lacritin to the ocular surface has been found to rescue the normal corneal sensory neural dry and wet responses necessary for normal eye physiology. Since all glands wetting the eye are regulated by the reflex arc downstream of corneal sensory input, lacritin or lacritin fragments, synthetic peptides or mimetics should benefit all forms of dry eye. Preclinical studies in rabbits and in dry eye mice models imply that it may also restore the density of corneal sensory innervation that decreases in dry eye. In contrast, commonly used 'artificial tears' temporarily alleviate symptoms without addressing cause.

It is disclosed herein that aqueous deficient dry eye tears are associated with decreased lacritin monomer, increased lacritin-C splice variant, less deglycanated SDC1, increased 25 kDa SDC1 fragment, and decreased latent heparanase and increased active heparanase. Therefore, the present invention provides compositions and methods for detecting and diagnosing dry eye and for developing and providing treatment regimens for subjects found to have dry eye using one or more of the markers of dry eye disclosed herein. The present application provides compositions and methods for detecting and diagnosing dry eye, including the FOXO3 translocation assay disclosed herein. Multiple methods are also available and described for detecting and measuring the protein and protein fragments useful for detecting and diagnosing eye.

The present invention further provides for the use of lacritin, or biologically active fragments or homologs thereof, to sensitize corneal sensory nerves to drying of the surface of the eye and increases the neural wet response. In one embodiment, use of topical lacritin or fragment N-94 (SEQ ID NO: 7) restores or increases tearing. In one aspect, the use restores basal tearing. In one aspect, topical administration of lacritin suppresses lacrimal gland inflammation.

In accordance with one embodiment a method of treatment is provided to restore the levels of 90 kDa syndecan-1 (SDC1) or other deglycanated forms of syndecan-1 in the tears of a subject with dry eye. Restoring SDC1 enhances activity of lacritin that is present. The present invention further provides methods of treating dry eye using inhibitors of transglutaminase (TGM), which can be inhibitors of TGM activity or levels or synthesis.

In accordance with one embodiment, a composition is provided comprising a peptide, a non-native peptide, or a peptidomimetic derivative, comprising a sequence selected from the group consisting of SEQ ID NO: 1, SEQ ID NO: 5, SEQ ID NO: 6, SEQ ID NO: 7 and SEQ ID NO: 8 or a sequence that differs from SEQ ID NO: 1, SEQ ID NO: 5, SEQ ID NO: 6, SEQ ID NO: 7 and SEQ ID NO: 8 by 1, 2, 3, 4 or 5 amino acids, or a biologically active fragment, homolog, or derivative thereof. In one embodiment a peptide differs from SEQ ID NO: 1, SEQ ID NO: 5, or SEQ ID NO: 7 by 1, 2, 3, 4 or 5 conservative amino acid substitutions. In one embodiment, the amino acid modifications are amino acid substitution, and in one embodiment the substitutions are conservative amino acid substitutions.

In some embodiments, the peptide of the present disclosure comprises an amino acid sequence which has at least 75%, 80%, 85%, 90% or 95% sequence identity to amino acid sequence SEQ ID NO: 1, SEQ ID NO: 5, or SEQ ID NO: 7 or a biologically active fragment, homolog, or derivative thereof.

In some embodiments, the peptide of the present disclosures comprises a non-native amino acid sequence which has at least 75%, 80%, 85%, 90% or 95% sequence identity to amino acid sequence SEQ ID NO: 1, SEQ ID NO: 5, or SEQ ID NO: 7 or a peptidomimetic derivative of SEQ ID NO: 1, SEQ ID NO: 5 or SEQ ID NO: 7. The statement that the peptide is a non-native is intended to exclude the native peptides of parent lacritin proteins.

In accordance with one embodiment a method of enhancing corneal wound healing in a subject in need thereof is provided. The method comprises contacting an ocular surface of said subject with a composition comprising lacritin or a bioactive fragment thereof. In one embodiment the bioactive fragment of lacritin is selected from the group consisting of
KQFIENGSEFAQKLLKKFS (SEQ ID NO: 5);
KQFIENGSEFAQKLLKKFSLLKPWA (SEQ ID NO: 7);
KQFIENGSEFANKLLKKFS (SEQ ID NO: 6); and
KQFIENGSEFANKLLKKFSLLKPWA (SEQ ID NO: 8)
or a derivative thereof that differs from SEQ ID NO: 5, SEQ ID NO: 6, SEQ ID NO: 7 or SEQ ID NO: 8 by one or two amino acid substitutions. In one embodiment the subject is recovering from PRK (photorefractive keratectomy) or LASIK (Laser-Assisted in situ Keratomileusis) surgery.

In another embodiment a bactericidal composition is provided, comprising a C-terminal fragment of lacritin. In one embodiment the fragment is a peptide selected from SEQ ID NO: 5, SEQ ID NO: 6, SEQ ID NO: 7, or SEQ ID NO: 8 or a derivative thereof that differs from SEQ ID NO: 5, SEQ ID NO: 6, SEQ ID NO: 7 or SEQ ID NO: 8 by one or two amino acid substitutions. In one embodiment the fragment is a peptide consisting of the sequence of SEQ ID NO: 7. In one embodiment the composition comprises a pharmaceutically acceptable carrier wherein the composition is suitable for topical administration to an ocular surface of a subject. In one embodiment the composition, further comprises a second anti-bacterial agent. As disclosed herein a method of treating a corneal infection is provided wherein the method comprises contacting the cornea of a subject in need thereof with the composition comprising a C-terminal fragment of lacritin.

BRIEF DESCRIPTION OF THE DRAWINGS

FIG. 2A is a Western blot demonstrating the detection of lacritin-C using mab 4F6. Lacritin-C splice variant is constantly elevated in dry eye. FIG. 2B is a Western blot using secondary antibody alone and serves as a negative control. No bands are detected using only the secondary antibody.

FIG. 3A is a Western blot demonstrating the detection of heparanase using #1453 antibody. Latent heparanase is indicated by ~75 kDa band; active heparanase indicated by ~50 kDa band. FIG. 3B is a Western blot demonstrating the detection of heparanase using #753 antibody.

FIG. 6A presents immunoblots of protease sensitive positive control 'SN pep' from a different protein, and LACRIPEP ('N-94'; SEQ ID NO: 7), after incubation in lacritin-depleted human tears for 2-16 hr at 37° C. FIG. 6B presents mass spectrometric analysis, wherein the top row presents MS profiles of SN pep, LACRIPEP ('N-94'), and LACRIPEP without six C-terminal amino acids ('N-94/C-6') prior to addition to tears and the 37° C. incubation step, and the bottom row provides MS profiles after incubation in lacritin depleted tears for 4 hr at 37° C.

FIG. 7B) relative to an inactive lacritin fragment control (C-25D).

FIG. 9 Alignment of the 25 amino acid C-terminal fragments of lacritin homologs from primate species including human (SEQ ID NO: 7); Chimpanzee (SEQ ID NO: 17); Bushbaby (SEQ ID NO: 18); Gorilla (SEQ ID NO: 19); Macaque (SEQ ID NO: 20); Marmoset (SEQ ID NO: 21);

Figure 1:
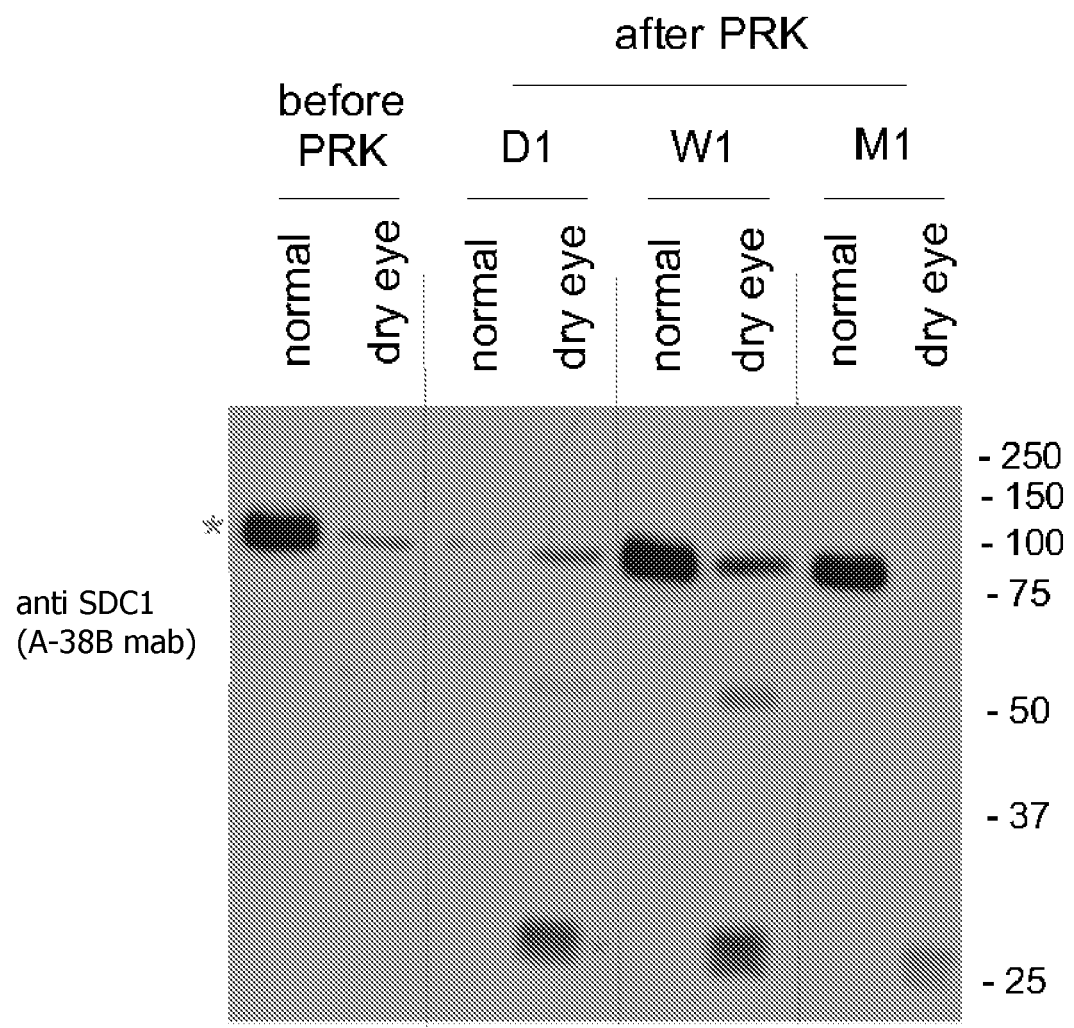
FIG. 1. Detection of rare, deglycanated and 25 kDa forms of syndecan-1 respectively in normal and dry eye tears. Left paired samples (before photorefractive keratectomy (PRK) or Laser-Assisted in situ Keratomileusis (LASIK)) ~90 kDa deglycanated SDC1 is abundant in normal tears and barely detectable in dry eye tears. Day 1 (D1) after PRK or LASIK surgery, ~90 kDa deglycanated SDC1 is less than in dry eye tears. Also, a 25 kDa SDC1 fragment is apparent in dry eye tears. Surgery promotes dry eye by severing corneal sensory nerves. Week 1 (W1) after PRK or LASIK surgery, the ~90 deglycanated SDC1 level is restored in normal tears that received surgery, and 25 kDa level in dry eye tears remains elevated (less at 1 Month (M1).

Mouse Lemur (SEQ ID NO: 22) and Orangutan (SEQ ID NO: 23) demonstrating a high sequence conservation between primate species.

DETAILED DESCRIPTION

Abbreviations and Acronyms

FACS means fluorescence activated cell sorter
HCE means human corneal epithelial
HPSE means heparanase
HS means heparan sulfate
HSG means human salivary gland
INFG means interferon gamma (also referred to as IFNG)
IRB means institutional review board
SDC1 means syndecan-1
TGM means transglutaminase
TNF means tumor necrosis factor Definitions In describing and claiming the invention, the following terminology will be used in accordance with the definitions set forth below.

As used herein, the term "lacritin polypeptide" and the like terms is defined as any peptide comprising the amino acid sequence SEQ ID NO: 1 and or a biologically active fragment, homolog, or derivative thereof. As used herein, the term "biologically active fragments" or "bioactive fragment" of a lacritin polypeptide encompasses natural or synthetic portions of the amino acid sequence MKFTTLLFLAAVAGALVYAEDASSDSTGADPAQEAGTSKPNEEISGPAEPASPPETTTTAQETSAAAVQGTAKVTSSRQELNPLKSIVEKSILLTEQALAKAGK GMHGGVPGGKQFIENGSEFAQKLLKKFSLLKPWA (SEQ ID NO: 1). Fragments of lacritin (SEQ ID NO: 1) include, for example: KQFIENGSEFAQKLLKKFS (SEQ ID NO: 5) ('N-94/C-6') (Wang et al., (2006) J. Cell Biol. 174, 689-700). and KQFIENGSEFAQKLLKKFSLLKPWA (SEQ ID NO: 7) ('N-94') (see Zhang et al., (2013) J. Biol. Chem. 288, 12090-12101).

The term "about," as used herein, means approximately, in the region of, roughly, or around. When the term "about" is used in conjunction with a numerical value or range, it modifies that range by extending the boundaries above and below the numerical values set forth. For example, in one aspect, the term "about" is used herein to modify a numerical value above and below the stated value by a variance of 20%, but is not intended to designate any value or range of values to only this broader definition. Each value or range of values preceded by the term "about" is also intended to encompass the embodiment of the stated absolute value or range of values.

As used herein an "acylated" amino acid is an amino acid comprising an acyl group which is non-native to a naturally-occurring amino acid, regardless by the means by which it is produced. Exemplary methods of producing acylated amino acids and acylated peptides are known in the art and include acylating an amino acid before inclusion in the peptide or peptide synthesis followed by chemical acylation of the peptide. In some embodiments, the acyl group causes the peptide to have one or more of (i) a prolonged half-life in circulation, (ii) a delayed onset of action, (iii) an extended duration of action, and (iv) an improved resistance to proteases.

As used herein, an "alkylated" amino acid is an amino acid comprising an alkyl group which is non-native to a naturally-occurring amino acid, regardless of the means by which it is produced. Exemplary methods of producing alkylated amino acids and alkylated peptides are known in the art and including alkylating an amino acid before inclusion in the peptide or peptide synthesis followed by chemical alkylation of the peptide. Without being held to any particular theory, it is believed that alkylation of peptides will achieve similar, if not the same, effects as acylation of the peptides, e.g., a prolonged half-life in circulation, a delayed onset of action, an extended duration of action, and an improved resistance to proteases.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

As used herein, the term "hydrophilic moiety" refers to any compound that is readily water-soluble or readily absorbs water, and which are tolerated in vivo by mammalian species without toxic effects (i.e. are biocompatible). Examples of hydrophilic moieties include polyethylene glycol (PEG), polylactic acid, polyglycolic acid, a polylactic-polyglycolic acid copolymer, polyvinyl alcohol, polyvinylpyrrolidone, polymethoxazoline, polyethyloxazoline, polyhydroxyethyl methacrylate, polyhydroxypropyl methacrylamide, polymethacrylamide, polydimethylacrylamide, and derivatised celluloses such as hydroxymethylcellulose or hydroxyethylcellulose and co-polymers thereof, as well as natural polymers including, for example, albumin, heparin and dextran.

A "subject" of experimentation, diagnosis or treatment is an animal, including a human.

As used herein the term "Dry eye" (or Dry Eye) encompasses any condition in which there are insufficient tears to lubricate and nourish the eye. Subjects with dry eyes either do not produce enough tears or have a poor quality of tears. Dry eye as used herein includes, but is not limited to: aqueous-deficient and evaporative dry eye. Aqueous-deficient dry eye includes, but is not limited to, Sjogren's Syndrome Dry Eye (including primary and secondary), Non-Sjogren's Dry Eye (including lacrimal deficiency, lacrimal gland duct obstruction, reflex block, and from systemic drugs). Evaporative dry eye includes, but is not limited to, Intrinsic (including meibomian oil deficiency, disorders of the lid aperture, low blink rate, and resulting from the drug action of Accutane) and Extrinsic (including Vitamin A deficiency, topical drug preservatives, contact lens wear, and ocular surface disease (such as allergies).

As used herein, the term "treating" includes prophylaxis of the specific disorder or condition, or alleviation of the symptoms associated with a specific disorder or condition and/or preventing or eliminating said symptoms. For example, as used herein the term "treating dry eye" will refer in general to maintaining basal tear levels near normal levels and may include increasing tear levels depending on a given situation.

As used herein an "effective" amount or a "therapeutically effective amount" of a pharmaceutical agent refers to a nontoxic but sufficient amount of an agent to provide the desired effect. For example one desired effect would be the prevention or treatment of dry eye. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid/nucleic acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J. Mol. Biol. 215:403-410) are available for determining sequence identity.

As used herein an amino acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln, cysteic acid and homocysteic acid;
III. Polar, positively charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine The term "isolated" as used herein means having been removed from its natural environment. In some embodiments, a peptide is made through recombinant methods and the peptide is isolated from the host cell.

The term "purified," as defined herein means the isolation of a molecule or compound in a form that is substantially free of contaminants normally associated with the molecule or compound in a native or natural environment and means having been increased in purity as a result of being separated from other components of the original composition. The term "purified polypeptide" is used herein to describe a polypeptide which has been separated from other compounds including, but not limited to nucleic acid molecules, lipids and carbohydrates.

A "peptidomimetic" refers to a chemical compound having a structure that is different from the general structure of an existing peptide, but that functions in a manner similar to the existing peptide, e.g., by mimicking the biological activity of that peptide. Peptidomimetics typically comprise naturally-occurring amino acids and/or unnatural amino acids, but can also comprise modifications to the peptide backbone. For example a peptidomimetic may include a sequence of naturally-occurring amino acids with the insertion or substitution of a non-peptide moiety, e.g. a retroinverso fragment, or incorporation of non-peptide bonds such as an azapeptide bond (CO substituted by NH) or pseudopeptide bond (e.g. NH substituted with $CH_2$), or an ester bond (e.g., depsipeptides, wherein one or more of the amide (—CONHR—) bonds are replaced by ester (COOR) bonds). Alternatively the peptidomimetic may be devoid of any naturally-occurring amino acids.

As use herein, the terms "administration of" and or "administering" a compound should be understood to mean providing a compound of the invention to a subject in need of treatment.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein the term "amino acid" encompasses any molecule containing both amino and carboxyl functional groups, wherein the amino and carboxylate groups are attached to the same carbon (the alpha carbon). The alpha carbon optionally may have one or two further organic substituents. For the purposes of the present disclosure designation of an amino acid without specifying its stereochemistry is intended to encompass either the L or D form of the amino acid, or a racemic mixture. However, in the instance where an amino acid is designated by its three letter code and includes a superscript number, the D form of the amino acid is specified by inclusion of a lower case d before the three letter code and superscript number (e.g., dLys1), wherein the designation lacking the lower case d (e.g., Lys1) is intended to specify the native L form of the amino acid. In this nomenclature, the inclusion of the superscript number designates the position of the amino acid in the peptide sequence numbered consecutively from the N-terminus. The expression "amino acid" as used herein is meant to include both natural and synthetic amino acids, and both D and L amino acids. "Standard amino acid" means any of the twenty L-amino acids commonly found in naturally occurring peptides.

As used herein the term "non-coded amino acid" encompasses any amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr, regardless of whether it is prepared synthetically or derived from a natural source.

As used herein a general reference to a peptide is intended to encompass peptides that have modified amino and carboxy termini, including but not limited to salts. For example, an amino acid sequence designating the standard amino acids is intended to encompass standard amino acids at the N- and C-terminus as well as a corresponding hydroxyl acid at the N-terminus and/or a corresponding C-terminal amino acid modified to comprise an amide group in place of the terminal carboxylic acid. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies.

An "antimicrobial agent," as used herein, refers to any compound which impedes the growth of any microbes, or kills such microbes.

A "bactericidal agent," as used herein, refers to any compound which impedes the growth of bacteria, or kills bacteria.

As used herein, the term "biologically active fragments" or "bioactive fragment" of the polypeptides encompasses natural or synthetic portions of the full length protein that are capable of specific binding to their natural ligand or of performing the function of the protein.

As used herein, the terms "complementary" or "complementarity" are used in reference to polynucleotides (i.e., a sequence of nucleotides) related by the base pairing rules. For example, for the sequence "AGT," is complementary to the sequence "TCA."

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence polarization or altered light scattering.

As used herein, the phrase "enhancing survival" refers to decreasing the amount of death, or the rate of death, in a cell population. Enhancing survival can be due to preventing cell death alone (e.g., cell death in conjunction with apoptosis), or decreasing the rate of cell death. The decrease in cell death can also result from indirect effects such as inducing proliferation of some cells, such indirect effect effectively replenishing at least some or all of a population of cells as they die. Enhancing survival of cells can also be accomplished by a combination of inducing proliferation and decreasing cell death, or the rate of cell death. "Promoting survival" and "enhancing survivability" are used interchangeably with "enhancing survival" herein.

A "fragment" or "segment" is a portion of an amino acid sequence, comprising at least one amino acid, or a portion of a nucleic acid sequence comprising at least one nucleotide. The terms "fragment" and "segment" are used interchangeably herein. A fragment of a lacritin peptide which is used herein as part of a composition for use in a treatment or to elicit a lacritin effect is presumed to be a biologically active fragment for the response to be elicited.

As used herein, a "functional" biological molecule is a biological molecule in a form in which it exhibits a property or activity by which it is characterized. A functional enzyme, for example, is one which exhibits the characteristic catalytic activity by which the enzyme is characterized.

As used herein, a "gene" refers to the nucleic acid coding sequence as well as the regulatory elements necessary for the DNA sequence to be transcribed into messenger RNA (mRNA) and then translated into a sequence of amino acids characteristic of a specific polypeptide.

As used herein, the term "insult" refers to contact with a substance or environmental change that results in an alteration of normal cellular metabolism in a cell or population of cells. Environmental insults may include, but are not limited to, chemicals, environmental pollutants, heavy metals, viral or bacterial infections, changes in temperature, changes in pH, as well as agents producing oxidative damage, DNA damage, or pathogenesis. The term "insult" is used interchangeably with "environmental insult" herein.

As used herein, the term "syndecan-1" refers to peptides comprising the amino acid sequence of SEQ ID NO: 2 and biologically active fragments, derivatives, and homologs thereof. As used herein, the term "biologically active fragments" or "bioactive fragment" of a syndecan-1 polypeptide encompasses natural or synthetic portions of the amino acid sequence

```
                                         (SEQ ID NO: 2)
MRRAALWLWLCALALSLQPALPQIVATNLPPEDQDGSGDDSDNFSGSGAG

ALQDITLSQQTPSTWKDTQLLTAIPTSPEPTGLEATAASTSTLPAGEGPK

EGEAVVLPEVEPGLTAREQEATPRPRETTQLPTTHQASTTTATTAQEPAT

SHPHRDMQPGHHETSTPAGPSQADLHTPHTEDGGPSATERAAEDGASSQL

PAAEGSGEQDFTFETSGENTAVVAVEPDRRNQSPVDQGATGASQGLLDRK

EVLGGVIAGGLVGLIFAVCLVGFMLYRMKKKDEGSYSLEEPKQANGGAYQ

KPTKQEEFYA.
```

The underlined portion of SEQ ID NO: 2 represents "shed and deglycanated 90 kDa form of syndecan-1" (or 90 kDa deglycanated SDC-1), having the sequence:

```
                                         (SEQ ID NO: 3)
QIVATNLPPEDQDGSGDDSDNFSGSGAGALQDITLSQQTPSTWKDTQLLT

AIPTSPEPTGLEATAASTSTLPAGEGPKEGEAVVLPEVEPGLTAREQEAT

PRPRETTQLPTTHQASTTTATTAQEPATSHPHRDMQPGHHETSTPAGPSQ

ADLHTPHTEDGGPSATERAAEDGASSQLPAAEGSGEQDFTFETSGENTAV

VAVEPDRRNQSPVDQGATGASQGLLDRKE.
```

As used herein, the term "a 25 kDa fragment of SDC-1 ectodomain" (or 25 kDa SDC-1) refers to a 25 kDa fragment of SDC-1 that contains the amino acid sequence of residues 85-88 of SEQ ID NO: 3, the 90 kDa deglycanated SDC-1.

As used herein, the term "heparanase" refers to peptides comprising the amino acid sequence of SEQ ID NO: 4 and biologically active fragments, derivatives, and homologs thereof. As used herein, the term "biologically active fragments" or "bioactive fragment" of a heparanase polypeptide encompasses natural or synthetic portions of the amino acid sequence

```
                                         (SEQ ID NO: 4)
MLLRSKPALPPPLMLLLLGPLGPLSPGALPRPAQAQDVVDLDFFTQEP

LHLVSPSFLSVTIDANLATDPRFLILLGSPKLRTLARGLSPAYLRFGG

TKTDFLIFDPKKESTFEERSYWQSQVNQDICKYGSIPPDVEEKLRLEW

PYQEQLLLREHYQKKFKNSTYSRSSVDVLYTFANCSGLDLIFGLNALL
```

-continued
```
RTADLQWNSSNAQLLLDYCSSKGYNISWELGNEPNSFLKKADIFINGS

QLGEDFIQLHKLLRKSTFKNAKLYGPDVGQPRRKTAKMLKSFLKAGGE

VIDSVTWHHYYLNGRTATKEDFLNPDVLDIFISSVQKVFQVVESTRPG

KKVWLGETSSAYGGGAPLLSDTFAAGFMWLDKLGLSARMGIEVVMRQV

FFGAGNYHLVDENFDPLPDYWLSLLFKKLVGTKVLMASVQGSKRRKLR

VYLHCTNTDNPRYKEGDLTLYAINLHNVTKYLRLPYPFSNKQVDKYLL

RPLGPHGLLSKSVQLNGLTLKMVDDQTLPPLMEKPLRPGSSLGLPAFS

YSFFVIRNAKVAACI.
```

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow and Lane, 1988, Antibodies, A Laboratory Manual, Cold Spring Harbor Publications, New York, for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

"Ocular surface," as used herein, refers to the surface of the eye, particularly the corneal surface.

The phrase "ocular surface-associated disease, disorder, or condition," as used herein, refers to any disease, disorder or condition which directly or indirectly causes, or can cause, any of the problems or symptoms described herein regarding disease, disorders, or conditions of the ocular surface.

"Operably linked" refers to a juxtaposition wherein the components are configured so as to perform their usual function. Thus, control sequences or promoters operably linked to a coding sequence are capable of effecting the expression of the coding sequence.

A "marker" is an atom or molecule that permits the specific detection of a molecule comprising that marker in the presence of similar molecules without such a marker. Markers include, for example radioactive isotopes, antigenic determinants, nucleic acids available for hybridization, chromophors, fluorophors, chemiluminescent molecules, electrochemically detectable molecules, molecules that provide for altered fluorescence polarization or altered light scattering and molecules that allow for enhanced survival of an cell or organism (i.e. a selectable marker). A reporter gene is a gene that encodes for a marker.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

A "polylinker" is a nucleic acid sequence that comprises a series of three or more different restriction endonuclease recognitions sequences closely spaced to one another (i.e. less than 10 nucleotides between each site).

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein, "nucleic acid," "DNA," and similar terms also include nucleic acid analogs, i.e. analogs having other than a phosphodiester backbone. For example, the so called "peptide nucleic acids," which are known in the art and have peptide bonds instead of phosphodiester bonds in the backbone, are considered within the scope of the present invention.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH2-carbamate linkage (—CH2OC(O)NR—), a phosphonate linkage, a —CH2-sulfonamide (—CH2-S(O)2NR—) linkage, a urea (—NHC(O)NH—) linkage, a —CH2-secondary amine linkage, or with an alkylated peptidyl linkage (—C(O)NR—) wherein R is C1-C4 alkyl;

2. peptides wherein the N-terminus is derivatized to a —NRR1 group, to a —NRC(O)R group, to a —NRC(O)OR group, to a —NRS(O)2R group, to a —NHC(O)NHR group where R and R1 are hydrogen or C1-C4 alkyl with the proviso that R and R1 are not both hydrogen;

3. peptides wherein the C terminus is derivatized to —C(O)R2 where R 2 is selected from the group consisting of C1-C4 alkoxy, and —NR3R4 where R3 and R4 are independently selected from the group consisting of hydrogen and C1-C4 alkyl.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for tryptophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

The term "fusion polypeptide" or "fusion protein" refers to a chimeric protein containing a reference protein (e.g., lacritin) joined at the N- and/or C-terminus to one or more heterologous sequences (e.g., a non lacritin polypeptide, such as syndecan). Polypeptide molecules are said to have an "amino terminus" (N terminus) and a "carboxy terminus" (C terminus) because peptide linkages occur between the backbone amino group of a first amino acid residue and the backbone carboxyl group of a second amino acid residue. The terms "N terminal" and "C terminal" in reference to polypeptide sequences refer to regions of polypeptides including portions of the N terminal and C terminal regions of the polypeptide, respectively. A sequence that includes a portion of the N terminal region of polypeptide includes amino acids predominantly from the N terminal half of the polypeptide chain, but is not limited to such sequences. For example, an N terminal sequence may include an interior portion of the polypeptide sequence including bases from both the N terminal and C terminal halves of the polypeptide. The same applies to C terminal regions. N terminal and C terminal regions may, but need not, include the amino acid defining the ultimate N terminus and C terminus of the polypeptide, respectively.

The fusion proteins of the invention may be prepared by recombinant methods or by solid phase chemical peptide synthesis methods. Such methods have been known in the art since the early 1960's (Merrifield, 1963) (See also Stewart et al., Solid Phase Peptide Synthesis, 2 ed., Pierce Chemical Co., Rockford, Ill., pp. 11-12)) and have recently been employed in commercially available laboratory peptide design and synthesis kits (Cambridge Research Biochemicals). In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

The invention also includes a stable cell line that expresses a lacritin bioactive fragment or a lacritin/syndecan-1 fusion protein, as well as an expression cassette comprising a nucleic acid molecule encoding the lacritin fragment or lacritin/syndecan-1 fusion protein, and a vector capable of expressing the nucleic acid molecule of the invention in a host cell. Preferably, the expression cassette comprises a promoter, e.g., a constitutive or regulatable promoter, operably linked to the nucleic acid sequence. In one embodiment, the expression cassette contains an inducible promoter. Also provided is a host cell, e.g., a prokaryotic cell or an eukaryotic cell such as a plant or vertebrate cell, e.g., a mammalian cell, including but not limited to a human, non-human primate, canine, feline, bovine, equine, ovine or rodent (e.g., rabbit, rat, ferret or mouse) cell, which comprises the expression cassette or vector of the invention, and a kit which comprises the nucleic acid molecule, expression cassette, vector, host cell or lacritin/syndecan-1 fusion protein.

A "vector" is also meant to include a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, plasmids, cosmids, lambda phage vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

As used herein, the term "wound" relates to a physical tear or rupture to a tissue or cell layer. A wound may occur by any physical insult, including a surgical procedure.

Embodiments

As disclosed herein compositions having lacritin based activity are disclosed for treating an ocular surface-associated disease, disorder, or condition. In accordance with one embodiment a composition is provided comprising a lacritin polypeptide, a bioactive fragment of lacritin, a non-native lacritin peptide, or peptidomimetic derivative of lacritin. In one embodiment the composition comprises a sequence selected from the group consisting of SEQ ID NO: 1, SEQ ID NO: 7, SEQ ID NO: 8, SEQ ID NO: 5, and SEQ ID NO: 6 or a sequence that differs from SEQ ID NO: 1, SEQ ID NO: 7, SEQ ID NO: 8, SEQ ID NO: 5, or SEQ ID NO: 6 by 1, 2, 3, 4 or 5 amino acid modifications. In one embodiment the composition comprises a sequence selected from the group consisting of SEQ ID NO: 7 or SEQ ID NO: 8 or a sequence that differs from SEQ ID NO: 7 or SEQ ID NO: 8 by 1, 2, 3, 4 or 5 amino acid substitutions, and in a further embodiment the 1, 2, 3, 4 or 5 amino acid substitutions are conservative amino acid substitutions.

In one embodiment a composition is provided comprising a bioactive fragment of lacritin, wherein the bioactive fragment consists of the sequence of SEQ ID NO: 7 or a derivative that differs from SEQ ID NO: 7 by a single amino acid substitution. In one embodiment the single amino acid substitution is a conservative amino acid substation and in a further embodiment the amino acid substitution is at position 4, 6, 8, 10, 17 and 19. In one embodiment the bioactive fragment consists of the sequence of SEQ ID NO: 7 or a derivative that differs from SEQ ID NO: 7 by a single amino acid substitution at position 4 or 19. Surprisingly, applicants have found that the 25 amino acid C-terminal fragment of native human lacritin (SEQ ID NO: 7) has enhance stability in human tears relative to the same fragment having the terminal 6 amino acids removed (SEQ ID NO: 5). In particular, immunoblotting reveals that N-94/C-6 loses epitopes after incubation in lacritin depleted tears for 4 hr at 37° C. whereas Lacripep ('N-94'; SEQ ID NO: 7) does not.

Although topical application of ophthalmic products has remained the most popular and well-tolerated administration route for patient compliance, the bioavailability of eye drops is severely hindered by blinking, baseline and reflex lacrimation, and nasolacrimal drainage. One solution to enhance the therapeutic index of topical treatments is through the application of polymeric nanoparticles as drug carriers. In accordance with one embodiment a pharmaceutical composition is provided comprising lacritin, or a bioactive fragment thereof linked to a nanoparticle. In one embodiment the nanoparticle is a thermo-responsive elastin-like polypeptide (ELP). ELPs are composed of the repetitive pentapeptide motif (Val-Pro-Gly-Xaa-Gly)n (SEQ ID NO: 24) and exhibit unique reversible inverse phase transition temperatures, Tt, below which they solubilize and above which they phase separate. In one embodiment the carboxy terminus of lacritin or a bioactive fragment thereof is linked to an ELP and in one embodiment the C-terminus of a peptide consisting of SEQ ID NO: 5, SEQ ID NO: 6, SEQ ID NO: 7, or SEQ ID NO: 8 is linked to the repetitive pentapeptide motif $(VPGSG)_{48}(VPGIG)_{48}$ (SEQ ID NO: 28).

In accordance with one embodiment, a composition is provided comprising a syndecan-1 peptide, a non-native peptide, or a peptidomimetic derivative thereof. In one embodiment the peptide comprises a sequence selected from the group consisting of SEQ ID NO: 2 and SEQ ID NO: 3 or a sequence that differs from SEQ ID NO: 2 and SEQ ID NO: 3 by 1, 2, 3, 4 or 5 amino acids, and homologs and fragments thereof. In one embodiment a peptide differs from SEQ ID NO: 2 and SEQ ID NO: 3 by 1, 2, 3, 4 or 5 conservative amino acid substitutions. In one embodiment, the amino acid modifications are amino acid substitution, and in one embodiment the substitutions are conservative amino acid substitutions. In one embodiment the composition comprises a syndecan-1 fragment consisting of the sequence of SEQ ID NO: 2.

In some embodiments, the peptide of the present disclosure comprises an amino acid sequence which has at least 75%, 80%, 85%, 90% or 95% sequence identity to an amino acid sequence of SEQ ID NO: 2 or SEQ ID NO: 3 or a fragment or homolog thereof.

In some embodiments, the peptide of the present disclosures comprises a non-native amino acid sequence which has at least 75%, 80%, 85%, 90% or 95% sequence identity to an amino acid sequence of SEQ ID NO: 2 or SEQ ID NO:

3 or a peptidomimetic derivative of SEQ ID NO: 2 or SEQ ID NO: 3. The statement that the peptide is a non-native is intended to exclude the native peptides of parent proteins.

Compositions comprising a lacritin peptide or bioactive fragment or derivative thereof have use in treating ocular surface-associated diseases, disorders, and conditions, including dry eye. Accordingly, in one embodiment lacritin polypeptide comprising compositions are used to treat such diseases, disorders, and conditions.

In accordance with one embodiment, a composition is provided comprising a heparinase peptide, a non-native peptide, or a peptidomimetic derivative thereof, wherein the peptide comprises a sequence selected from the group consisting of SEQ ID NO: 4 or a sequence that differs from SEQ ID NO: 4 by 1, 2, 3, 4 or 5 amino acids, and homologs and fragments thereof. In one embodiment a heparinase peptide is provided that differs from SEQ ID NO: 4 by 1, 2, 3, 4 or 5 amino acid modifications. In one embodiment, the amino acid modifications are amino acid substitution, and in one embodiment the substitutions are conservative amino acid substitutions.

In some embodiments, the peptide of the present disclosure comprises an amino acid sequence which has at least 75%, 80%, 85%, 90% or 95% sequence identity to the amino acid sequence SEQ ID NO: 4 or a fragment or homolog thereof.

In some embodiments, the peptide of the present disclosure comprises a non-native amino acid sequence which has at least 75%, 80%, 85%, 90% or 95% sequence identity to an amino acid sequence of SEQ ID NO: 4 or a peptidomimetic derivative of SEQ ID NO: 4. The statement that the peptide is a non-native is intended to exclude the native peptides of parent proteins.

Derivatives of the peptides disclosed herein, in one embodiment, contain an amino acid sequence wherein 1, 2, or 3 amino acids are deleted, substituted or added, relative to the parent peptide, as long as the modified peptide has an activity equivalent to that of peptide having the aforementioned amino acid sequence.

In another embodiment, a novel, isolated polypeptide having an amino acid sequence of SEQ ID NO: 5, SEQ ID NO: 6, SEQ ID NO: 7, or SEQ ID NO: 8 or a biologically active fragment, homolog, or derivative thereof is provided. In one embodiment the polypeptide has an amino acid sequence SEQ ID NO: 5 or a biologically active fragment, homolog, or derivative thereof. In another embodiment, the polypeptide has amino acid sequence SEQ ID NO: 6. In another embodiment, the polypeptide has amino acid sequence SEQ ID NO: 7 or a biologically active fragment, homolog, or derivative thereof. In another embodiment, the polypeptide has amino acid sequence SEQ ID NO: 8 or a biologically active fragment, homolog, or derivative thereof.

In another embodiment, the present invention provides an isolated polypeptide comprising amino acid sequence SEQ ID NO: 5, SEQ ID NO: 6, SEQ ID NO: 7, or SEQ ID NO: 8 or a biologically active fragment, homolog, or derivative thereof for use in therapy. In one embodiment, the present invention provides an purified polypeptide comprising amino acid sequence SEQ ID NO: 5, SEQ ID NO: 6, SEQ ID NO: 7, or SEQ ID NO: 8 or a biologically active fragment, homolog, or derivative thereof for use in therapy. In one embodiment, the present invention provides a purified polypeptide consisting of the amino acid sequence of SEQ ID NO: 7 for use in treating an ocular surface-associated disease, disorder, or condition.

In another embodiment, the present invention provides for the use of an isolated polypeptide comprising amino acid sequence SEQ ID NO: 5, SEQ ID NO: 6, SEQ ID NO: 7, or SEQ ID NO: 8 or a biologically active fragment, homolog, or derivative thereof for the manufacture of a medicament for the treatment of an ocular surface-associated disease, disorder, or condition or any an indication recited herein. In one embodiment the polypeptide is a purified polypeptide consisting of the amino acid sequence of SEQ ID NO: 7.

In another embodiment, the present invention provides a novel pharmaceutical composition comprising a therapeutically effective amount of at least one polypeptide comprising amino acid sequence SEQ ID NO: 5, SEQ ID NO: 6, SEQ ID NO: 7, or SEQ ID NO: 8 or a biologically active fragment, homolog, or derivative thereof, wherein the composition is suitable for topical administration to an ocular surface of a subject.

In another embodiment, the composition comprises a polypeptide having amino acid sequence SEQ ID NO: 5 or a biologically active fragment, homolog, or derivative thereof. In another embodiment, the composition comprises a polypeptide having amino acid sequence SEQ ID NO: 6 or a biologically active fragment, homolog, or derivative thereof. In another embodiment, the composition comprises a polypeptide having amino acid sequence SEQ ID NO: 7 or a biologically active fragment, homolog, or derivative thereof. In another embodiment, the composition comprises a polypeptide having amino acid sequence SEQ ID NO: 8 or a biologically active fragment, homolog, or derivative thereof.

In one embodiment, a composition of the invention further comprises a carrier. In one aspect, the carrier is buffered saline. In one aspect, a composition of the invention is a pharmaceutical composition. In one aspect, a pharmaceutical composition of the invention comprises a pharmaceutically-acceptable carrier. In one aspect, the carrier is buffered saline. In one aspect, a pharmaceutical composition of the invention further comprises at least one additional therapeutic agent. In another embodiment, the composition further comprises buffered saline. In another embodiment, the buffer is phosphate buffer. In another embodiment, the buffer is selected from sodium phosphate, disodium phosphate, potassium phosphate, dipotassium phosphate, and a combination thereof.

In another embodiment, the composition further comprises a salt selected from NaCl and KCl. In another embodiment, the pH of the solution is selected from 7, 7.1, 7.2, 7.3, 7.4, 7.5, 7.6, 7.8, 7.9, and 8. In another embodiment, the pH is 7.4

An example of a buffered saline suitable for the present invention comprises $H_2O$ and the following components.

| Salt | Concentration mmol/L | Concentration g/L |
| --- | --- | --- |
| NaCl | 137 | 8.0 |
| KCl | 2.7 | 0.2 |
| $Na_2HPO_4$ | 10 | 1.44 |
| $KH_2PO_4$ | 1.8 | 0.24 |

In another embodiment, the present invention provides a novel method of treating dry eye, comprising contacting an ocular surface of a subject in need thereof with a composition the present invention. In accordance with one embodiment treatment with a lacritin based composition disclosed herein results in one or more of the following effects:

a) the treatment restores or increases tearing;

b) the treatment restores or increases tearing without causing or increasing inflammation;

c) the treatment restores basal tearing;
d) the treatment suppresses lacrimal gland inflammation;
e) the treatment diminishes the susceptibility of the eye to corneal staining;
f) the treatment diminishes tear osmolarity;
g) the treatment improves ocular surface health;
h) the treatment stimulates lacrimal glands;
i) the treatment stimulates meibomian glands;
j) the treatment stimulates conjunctival goblet cells;
k) the treatment stimulates corneal sensory nerves;
l) the treatment increases the level of a shed and deglycanated 90 kDa form of syndecan-1 in the tears of the treated subject;
m) the treatment decreases the level of a 25 kDa fragment of SDC-1 ectodomain in the tears of the treated subject;
n) the treatment decreases the level of inactive lacritin-C splice variant in the tears of the treated subject;
o) the treatment increases the level of latent heparanase in the tears of the treated subject; and
p) the treatment decreases the level of activated heparanase in the tears of the treated subject.

Patients suitable for treatment using a lacritin containing composition include patients having one or more of the following conditions:

a) the tears of the subject, prior to treatment, contain low levels of 90 kDa deglycanated SDC-1 compared to normal, non-dry eye tears;
b) the tears of the subject, prior to treatment, contain elevated levels of 25 kDa SDC-1 compared to normal, non-dry eye tears;
c) the tears of the subject, prior to treatment, contain elevated levels of inactive lacritin-C splice variant compared to normal, non-dry eye tears;
d) the tears of the subject, prior to treatment, contain low levels of latent heparanase compared to normal, non-dry eye tears;
e) the tears of the subject, prior to treatment, contain elevated levels of activated heparanase compared to normal, non-dry eye tears; and
f) the subject is recovering from PRK (photorefractive keratectomy) or LASIK (Laser-Assisted in situ Keratomileusis) surgery or other surgical procedure of the eye, and includes any subject who underwent PRK or LASIK surgery and is suffering from dry eye, regardless of the time since receiving the surgery. In one embodiment a subject having undergone PRK or LASIK surgery within the past day, month, six months, year, or even years can receive benefit from treatment using a lacritin containing formulation as disclosed herein.

In accordance with one embodiment a method for identifying a subject afflicted with insufficient tears to lubricate and nourish the eye, deriving from either insufficient tear quantity or have a poor quality of tears. In one embodiment the method comprises screening a tear sample obtained from said subject for the presence of at least one protein selected from the group consisting of latent heparanase/active heparanase;
90 kDa deglycanated SDC-1;
25 kDa SDC-1; and
inactive lacritin-C splice variant, wherein the concentration of latent heparanase, or active heparanase, and 90 kDa deglycanated SDC-1 is measured, and a decreased level of latent heparanase, or increase in active heparanase, (relative to levels present in tears from a normal eye) and/or a decreased level of 90 kDa deglycanated SDC-1 (relative to levels present in tears from a normal eye) and/or detection of 25 kDa SDC-1 in the tear sample, and/or detection of inactive lacritin-C splice variant in the tear sample identifies subjects having dry eye. Detection of any one of the individual four conditions or any combination thereof indicates a subject suffering from dry eye that would could benefit from the topical administration of a composition comprising a lacritin polypeptide, including for example the lacritin fragment of SEQ ID NO: 7.

In accordance with one embodiment a tear sample is obtained from a subject and the concentration of the 90 kDa deglycanated SDC-1 and 25 kDa SDC-1 are measured. Decreased levels of 90 kDa deglycanated SDC-1 coupled with increased levels of 25 kDa SDC-1, relative to concentrations of those peptides in tears from a normal eye, identifies subjects having dry eye. In one embodiment a tear sample is obtained from a subject and the sample is screened for the presence of 25 kDa SDC-1, wherein detection of 25 kDa SDC-1 identifies a subject having dry eye. In one embodiment a tear sample is obtained from a subject and the sample is screened for the presence of inactive lacritin-C splice variant, wherein detection of inactive lacritin-C splice variant identifies a subject having dry eye. In one embodiment a tear sample is obtained from a subject and the sample is screened for the presence of 25 kDa SDC-1 and inactive lacritin-C splice variant, wherein detection of 25 kDa SDC-1 and inactive lacritin-C splice variant identifies a subject having dry eye.

Advantageously, these markers of dry eye can serve as a basis for identifying subjects who will benefit from lacritin therapy. Accordingly, in one embodiment a method is provided for treating dry eye wherein the first step involves identifying those subjects suitable for treatment. In one embodiment the method of treating a subject for dry eye comprises obtaining a tear sample from the subject, and detecting the presence of at least one protein selected from the groups consisting of latent heparanase/active heparanase, 90 kDa deglycanated SDC-1, 25 kDa SDC-1, and inactive lacritin-C splice variant, wherein a decreased level of latent heparanase, or increase in active heparanase, (relative to levels present in tears from a normal eye), a decreased level of 90 kDa deglycanated SDC-1 (relative to tears from a normal eye), detection of 25 kDa SDC-1, and/or detection of inactive lacritin-C splice variant identifies subjects having dry eye. Those subjects identified as having dry eye based on detected levels of latent heparanase, active heparanase, 90 kDa deglycanated SDC-1, 25 kDa SDC-1, and/or inactive lacritin-C splice variant are then administered a composition comprising a lacritin polypeptide, including for example the peptide of SEQ ID NO: 7. More particularly, the ocular surface of the subject is contacted with a pharmaceutical composition comprising lacritin or a bioactive fragment thereof.

In accordance with one embodiment a subject identified as afflicted with dry eye is contacted with a bioactive fragment of lacritin selected from the group consisting of
KQFIENGSEFAQKLLKKFS (SEQ ID NO: 5);
KQFIENGSEFAQKLLKKFSLLKPWA (SEQ ID NO: 7);
KQFIENGSEFANKLLKKFS (SEQ ID NO: 6); and
KQFIENGSEFANKLLKKFSLLKPWA (SEQ ID NO: 8)
or a derivative thereof that differs from SEQ ID NO: 5, SEQ ID NO: 6, SEQ ID NO: 7 or SEQ ID NO: 8 by one or two amino acid substitutions. In one embodiment the bioactive fragment of lacritin consists of KQFIENGSEFAQKLLKKFSLLKPWA (SEQ ID NO: 7).

In accordance with one embodiment a subject afflicted with dry eye that is treatable with a lacritin therapy is identified by testing the tears of the subject for the presence of lacritin monomer, wherein a selective decrease in monomer compared to a control indicates for dry eye. The control is a subject (or group of subjects) not suffering from dry eye. In another embodiment a subject afflicted with dry eye that is treatable with a lacritin therapy is identified by testing the tears of the subject for the presence of 90 kDa deglycanated SDC-1, wherein the detection of normal levels of 90 kDa deglycanated SDC-1 does not indicate for dry eye. In another embodiment a subject afflicted with dry eye that is treatable with a lacritin therapy is identified by collecting the tears of the subject and separating the proteins of the tears via their weight. In one embodiment the proteins of tears are separated through the use of SDS-PAGE.

In another embodiment, testing is performed by contacting the tears of the subject with a test strip, comprising an agent capable of detecting the presence of 25 kDa SDC-1. In one embodiment the agent is an antibody, optionally a monoclonal antibody.

In another embodiment, testing is performed by contacting the tears of the subject with a test strip, comprising an agent capable of detecting the presence of 90 kDa deglycanated SDC-1. In one embodiment the agent is an antibody, optionally a monoclonal antibody.

In another embodiment, the tears are tested for the presence of 25 kDa SDC-1 and 90 kDa deglycanated SDC-1, wherein the presence of normal levels of 90 kDa deglycanated SDC-1 does not indicate for dry eye and the presence of 25 kDa SDC-1 indicates for dry eye. In another embodiment, the method of identifying patients afflicted with dry eye further comprises a step of treating the subject with a composition of the present invention. In one embodiment an ocular surface of a subject found to have 25 kDa SDC-1 in their tears is treated with a lacritin, or lacritin fragment, containing composition.

In another embodiment, the present invention provides a novel method of identifying a subject having dry eye, comprising testing the tears of the subject for the presence of 25 kDa SDC-1, wherein the presence of 25 kDa SDC-1 indicates for dry eye. In one embodiment, testing is performed by collecting the tears of the subject and separating the proteins of the tears based on their weight. In one embodiment the separation of the peptides is performed using SDS-PAGE.

In another embodiment, a novel method of identifying a subject having dry eye is provided wherein the tears of the subject are tested for the presence of inactive lacritin-C splice variant, wherein the presence of inactive lacritin-C splice variant indicates for dry eye. In one embodiment the presence of inactive lacritin-C splice variant is detected by collecting the tears of the subject and separating the proteins of the tears via their weight. In one embodiment the proteins of the tears are separated through the use of g SDS-PAGE. In another embodiment, testing is performed by contacting the tears of the subject with a test strip, comprising an agent capable of detecting the presence of inactive lacritin-C splice variant. In one embodiment the agent is an antibody, optionally a monoclonal antibody. In a further embodiment a method of treatment is provided comprising contacting an ocular surface of a subject found to have inactive lacritin-C splice variant in their tears with a composition of the present invention. invention.

In another embodiment, a novel method of identifying a subject having dry eye comprises testing the tears of the subject for the presence of active and latent heparanase, wherein the presence of elevated active heparanase or depressed latent heparanase indicates for dry eye. In one embodiment the testing is performed by collecting the tears of the subject and separating the proteins of the tears via their weight and blotting with an anti-heparanase antibody capable of detecting latent and active heparanase.

In one embodiment, a subject suffering from evaporative dry eye, corneal inflammation, or corneal ulceration is treated by contacting the cells of a subject in need thereof with a lacritin polypeptide comprising composition disclosed herein.

In another embodiment, the present invention provides a novel method of enhancing the proliferation of human corneal epithelial cells or lacrimal acinar cells, wherein the method comprises contacting the cells of a subject in need thereof with a composition of the present invention. In one embodiment the lacritin peptide compositions disclosed herein are used to enhance the proliferation of the subject's corneal epithelial cells, enhance the proliferation of the subject's lacrimal acinar cells or inhibit epithelial cell apoptosis or other forms of epithelial cell death. In one embodiment the method comprises contacting the cells of a subject in need thereof with a lacritin peptide composition disclosed herein, wherein the cells are selected from the corneal cells, conjunctival cells, or a combination of both.

In another embodiment, the epithelial cell cells contacted with a lacritin peptide have been subjected to an insult. In one embodiment the lacritin peptide consists of the sequence of SEQ ID NO: 7. In one embodiment, the insult is selected from the group consisting of blepharitis, dry eye, conjunctivitis, Sjogren's syndrome, corneal abrasion, ulceration, bacterial infection, direct trauma, surgery, radiant energy, ionizing energy, viral infection, fungal infection, parasitic infection, keratitis, systemic dermatologic disorders, collagen vascular diseases, Reiter's disease, and Behcet's disease.

In another embodiment a method of treating the diseases of lysosomal clearing is provided wherein the method comprises contacting an ocular surface of a subject with a composition of the present disclosure. In one embodiment, the diseases are selected from glaucoma and age-related macular degeneration (AMD). In one embodiment the method comprises contacting an ocular surface of a subject with a composition comprising a lacritin peptide, wherein the peptide consists of the sequence of SEQ ID NO: 7.

In another embodiment, the present invention relates to the treatment of diseases of lysosomal clearing. Such diseases include: glaucoma, age-related macular and degeneration (AMD). While not wishing to be bound by scientific theory, it is believed that lacritin triggers the autophagic capture and lysosomic degradation of intracellular aggregated (toxic) proteins in stressed cells. In AMD, the buildup of 'drusen' is both intracellular in retinal pigment epithelial cells and extracellular nearby these cells. It is expected that if a topical administration of a polypeptide of the present invention (e.g., lacritin or polypeptide of SEQ ID NO: 5, SEQ ID NO: 6, SEQ ID NO: 7, or SEQ ID NO: 8) infiltrates deep into the eye it will stimulate RPE autophagy to deplete drusen. In open angle glaucoma, stress in the trabecular meshwork cells leads to build up of intracellular material that accumulates. Although autophagy is chronically elevated, this is unhealthy for cells. Instead, lacritin forces a rapid and transient bolus of accelerated autophagy sufficient to clear offending accumulating protein. Autophagy then returns to baseline. A polypeptide of the present disclosure is expected to gain access to these cells. In another embodiment, the present invention provides a novel bactericidal composition. In accordance with one embodiment a bactericidal composition is provided comprising a C-terminal fragment of lacritin selected from SEQ ID NO: 5, SEQ ID NO: 6, SEQ ID NO: 7, or SEQ ID NO: 8 or a derivative thereof that differs from SEQ ID NO: 5, SEQ ID NO: 6, SEQ ID NO: 7 or SEQ ID NO: 8 by 1, 2, or 3 amino acid substitutions. In one embodiment the composition is suitable for topical administration to an ocular surface of a subject. In one embodiment the lacritin derivative that differs from SEQ ID NO: 5, SEQ ID NO: 6, SEQ ID NO: 7 or SEQ ID NO: 8 by 1, 2 or 3 amino acid substitutions, has amino acid substitutions located at positions selected from positions 4, 6, 8, 10, 17 and 19 relative to the numbering of SEQ ID NO: 7. These positions show variability among the highly conserved C-terminal regions of primate species (see FIG. 9). In one embodiment the lacritin derivative differs from SEQ ID NO: 7 or SEQ ID NO: 8 by 1 or 2 amino acid substitutions at positions 4 and/or 19 relative to the numbering of SEQ ID NO: 7. In one embodiment the amino acid substitutions are conservative amino acid substitutions. In accordance with one embodiment a bactericidal composition is provided comprising a C-terminal fragment of lacritin selected from SEQ ID NO: 5, SEQ ID NO: 6, SEQ ID NO: 7, or SEQ ID NO: 8. In accordance with one embodiment a bactericidal composition is provided comprising a C-terminal fragment of lacritin selected from SEQ ID NO: 7, or SEQ ID NO: 8, and in one embodiment the C-terminal fragment of lacritin consists of KQFIENGSEFAQKLLKKFSLLKPWA (SEQ ID NO: 7).

In one embodiment a bactericidal composition is provided comprising a first anti-bacterial agent, which is a polypeptide comprising the amino acid sequence of SEQ ID NO: 5, SEQ ID NO: 6, SEQ ID NO: 7, or SEQ ID NO: 8 or a biologically active fragment, homolog, or derivative thereof, wherein the composition is suitable for topical administration to an ocular surface of a subject. In one aspect, the polypeptide has amino acid sequence SEQ ID NO: 5. In another aspect, the polypeptide has amino acid sequence SEQ ID NO: 6. In another aspect, the polypeptide has amino acid sequence SEQ ID NO: 7. In another aspect, the polypeptide has amino acid sequence SEQ ID NO: 8. In one aspect, the bactericidal composition further comprises a bactericidally-acceptable carrier.

In one embodiment the bactericidal composition further comprises a second anti-bacterial agent. In one embodiment, the composition further comprises an anti-microbial agent. Suitable ophthalmic anti-microbial agents are known to those skilled in the art and include those described in U.S. Pat. Nos. 5,300,296, 6,316,669, 6,365,636 and 6,592,907, the disclosures of which are incorporated herein. Examples of anti-microbial agents suitable for use in accordance with the present invention include benzalkonium chloride, benzethonium chloride, benzyl alcohol, chlorobutanol, chlorhexidine digluconate or diacetate, methyl and propyl hydroxybenzoate (parabens), phenylethyl alcohol, phenylmercuric acetate or nitrate, sorbic acid, and thimerosal.

In one embodiment a second anti-bacterial agent is present in the bactericidal composition and in one embodiment the second anti-bacterial agent is one that is naturally present in mammalian eyes. In one embodiment the second anti-bacterial agent is lysozyme. In accordance with one embodiment the bactericidal composition comprises a C-terminal fragment of lacritin and a second anti-bacterial agent, wherein the ratio of C-terminal fragment of lacritin and a second anti-bacterial agent is at least 2:1. In one embodiment the bactericidal composition comprises a C-terminal fragment of lacritin and lysozyme, wherein the weight ratio of lysozyme to the C-terminal fragment of lacritin is from 4:1 to 3:1. In one embodiment the C-terminal fragment of lacritin consists of KQFIENGSEFAQKLLKKFSLLKPWA (SEQ ID NO: 7).

In accordance with one embodiment, a method is provided for treating infections of the eye. The method comprises the step of topically administering a composition comprising a lacritin polypeptide to the eye. In another embodiment, the present invention provides a novel method of treating a corneal infection, comprising contacting the cornea of a subject in need thereof with a bactericidal composition of the present invention. In one embodiment a peptide consisting of the sequence of the KQFIENGSEFAQKLLKKFSLLKPWA (SEQ ID NO: 7) is used in the manufacture of a medicament for the treatment of dry eye or treatment of a corneal infection.

In another embodiment, a method of treating a subject suffering from dry eye by contacting an ocular surface of a subject found to have active heparanase in their tears with a composition of the present invention.

In another embodiment, the present invention provides a novel container comprising a composition of the present invention, wherein the composition is in the form of an eye drop and in a volume sufficient for 1 dosage. In another embodiment, the composition is in the form of an eye drop and in a volume sufficient for 1-2 dosages. In another embodiment, the composition is in the form of an eye drop and in a volume sufficient for up to 1 week, 2 weeks, 3 weeks, or 4 weeks. In another embodiment, the container is in the form of a single use ampule, a bottle formed to dispense drops of the composition, or a bottle comprising: a body and a cap, wherein an eye dropper connect to the cap or part of the cap.

The present invention can also be practiced using methods described in U.S. Pat. Nos. 7,648,964, 7,459,440, 7,320,870, and 7,932,227, and publications WO 98/27205 (Jacobs et al., published Jun. 25, 1998), Sanghi et al., 2001, J. Mol. Biol., 310:127, Wang et al., 2006, J. Cell Biol., 174(5):689-700, Epub 2006 Aug. 21, Ma et al., J. Cell Biol., 2006, 174:7: 1097-1106, Zhang et al., J. Biol. Chem., 2013, 288(17): 12090-101: Epub 2013 Mar. 15, the contents of which are incorporated by reference in their entirety herein.

Various aspects and embodiments of the invention are described in further detail below.

In accordance with one embodiment a novel mechanism for the molecular identification of dry eye disease is coupled with a restorative therapy that addresses cause. In one embodiment the method of identifying dry eye relates to the discovery that a ~90 KDa deglycanated form of syndecan-1 is abundant in tears of normal individuals but not individuals suffering from dry eye, whereas a ~25 kDa syndecan-1 fragment is detectable in dry, but not normal tears. Also disclosed herein is the discovery that topical lacritin, the agonist of deglycanated syndecan-1, sensitizes corneal sensory nerves to drying of the surface of the eye and increases the neural wet response. Accordingly, one embodiment of the present invention is directed to a method of identifying dry eye by detecting abnormally low levels of ~90 kDa and/or the presence of 25 kDa syndecan-1 in tears. Another embodiment is directed to a method of increasing the corneal neural dry and wet responses by administering topical lacritin or lacritin fragments, synthetic peptides or mimetics.

Current tear supplements are not popular with subjects, in part because the relief obtained from such products is very brief (less than 15 min). Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Examples of these treatment approaches are disclosed in U.S. Pat. No. 4,131,651 (Shah et al.), U.S. Pat. No. 4,370,325 (Packman), U.S. Pat. No. 4,409,205 (Shively), U.S. Pat. Nos. 4,744,980 and 4,883,658 (Holly), U.S. Pat. No. 4,914,088 (Glonek), U.S. Pat. No. 5,075,104 (Gressel et al.) and U.S. Pat. No. 5,294,607 (Glonek et al.) the disclosures of which are incorporated herein. Existing ophthalmic formulations may also include TGF-beta, corticosteroids, or androgens. All are non-specific for the eye and have systemic effects. In contrast, lacritin is highly restricted to the eye and is a natural constituent of human tears and the tear film.

An ophthalmic formulation comprising lacritin, or fragments, homologs, or derivatives thereof (for example, an artificial tear fluids containing lacritin), is highly desirable due to the activity of lacritin and its localized effects. In accordance with one embodiment of the invention, compositions comprising lacritin, or bioactive fragments thereof, are used to enhance corneal wound healing, and/or treat subjects having deficient tear output. The lacritin compositions of the present invention can be formulated using standard ophthalmic components, and preferably, the compositions are formulated as solutions, suspensions, and other dosage forms for topical administration. Aqueous solutions are generally preferred, based on ease of formulation, biological compatibility (especially in view of the malady to be treated, e.g., dry eye-type diseases and disorders), as well as a subject's ability to easily administer such compositions by means of instilling one to two drops of the solutions in the affected eyes. However, the compositions may also be suspensions, viscous or semi-viscous gels, or other types of solid or semi-solid compositions.

The compositions of the present invention may include surfactants, preservative agents, antioxidants, tonicity agents, buffers, preservatives, co-solvents and viscosity building agents. Various surfactants useful in topical ophthalmic formulations may be employed in the present compositions. These surfactants may aid in preventing chemical degradation of the lacritin polypeptide and also prevent the lacritin polypeptide from binding to the containers in which the compositions are packaged. Examples of surfactants include, but are not limited to: Cremophor.™. EL, polyoxyl 20 ceto stearyl ether, polyoxyl 40 hydrogenated castor oil, polyoxyl 23 lauryl ether and poloxamer 407 may be used in the compositions. Antioxidants may be added to compositions of the present invention to protect the lacritin polypeptide from oxidation during storage. Examples of such antioxidants include, but are not limited to, vitamin E and analogs thereof, ascorbic acid and derivatives, and butylated hydroxyanisole (BHA).

Existing artificial tears formulations can also be used as pharmaceutically acceptable carriers for the lacritin active agent. Thus in one embodiment, a lacritin polypeptide is used to improve existing artificial tear products for Dry Eye syndromes, as well as develop products to aid corneal wound healing. Examples of artificial tears compositions useful as carriers include, but are not limited to, commercial products, such as Tears Naturale™, Tears Naturale II™, Tears Naturale Free™, and Bion Tears™. (Alcon Laboratories, Inc., Fort Worth, Tex.). Examples of other phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Glonek et al.); the foregoing patents are incorporated herein by reference to the extent they disclose phospholipid compositions useful as phospholipid carriers of the present invention. In accordance with one embodiment an topical ophthalmic formulation is provided comprising a lacritin peptide consisting of the sequence of SEQ ID NO: 7 and a pharmaceutically acceptable carrier. In one embodiment the composition further comprises a phospholipid. In an alternative embodiment the composition further comprises a surfactant, preservative agent, antioxidant, tonicity agent, buffer, preservative, co-solvent and/or viscosity building agents.

Other compounds may also be added to the ophthalmic compositions of the present disclosure to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers. In general, the phospholipid carrier or artificial tears carrier compositions will exhibit a viscosity of 1 to 400 centipoises ("cps"). Preferred compositions containing artificial tears or phospholipid carriers and will exhibit a viscosity of about 25 cps.

Topical ophthalmic products are typically packaged in multidose form. Preservatives are thus required to prevent microbial contamination during use. Suitable preservatives include:

benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

Because the gene promoter regulating lacritin gene expression is the most specific of any previously described lacrimal gland gene, the regulatory elements of this gene could be used to express other gene products in the eye. In particular, the lacritin gene promoter can be operably linked to a wide variety of exogenous genes to regulate the expression of the gene products to the lacrimal gland and/or used as gene therapy to treat Dry Eye syndromes.

The peptides of the present disclosure may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxycarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide is purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include C1-C5 branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—NH2), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without effect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present disclosure also provides for analogs of proteins. Analogs can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. To that end, 10 or more conservative amino acid changes typically have no effect on peptide function. In accordance with one embodiment conservative amino acid substitutions can include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2,3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from C1-C10 branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, Guide to Protein Purification, Harcourt Brace Jovanovich, San Diego).

The invention also includes a kit comprising the composition of the invention and an instructional material which describes administering the composition to a subject. In another embodiment, this kit comprises a (preferably sterile) solvent suitable for dissolving or suspending the composition of the invention prior to administering the composition.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, and to birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, intravenous, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

Formulations suitable for topical administration include, but are not limited to, liquid or semi liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1 1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference. Typically, dosages of the compound of the invention which may be administered to a subject, preferably a human, range in amount from 1 µg to about 100 g per kilogram of body weight of the subject. While the precise dosage administered will vary depending upon any number of factors, including but not limited to, the type of subject and type of disease state being treated, the age of the subject and the route of administration.

The invention further provides for identifying a subject with dry eye. For example, proteins or peptides found in tears can be detected using various methods, included, but not limited to, ELISA, immunoassay, immunofluorescence, immunohistochemistry, immunoprecipitation, and western blot, In one embodiment a kit is provided comprising the composition of the invention and an instructional material which describes administering the composition to a cell or a tissue of a subject. In another embodiment, this kit comprises a (preferably sterile) solvent suitable for dissolving or suspending the composition of the invention prior to administering the compound to the subject. As used herein, an "instructional material" includes a publication, a recording, a diagram, or any other medium of expression which can be used to communicate the usefulness of the peptide of the invention in the kit for effecting alleviation of the various diseases or disorders recited herein. In one embodiment the kit provides standard curves providing information regarding the concentration of various peptides in a normal healthy eye. Optionally, or alternately, the instructional material may describe one or more methods of alleviation the diseases or disorders in a cell or a tissue of a subject. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

Example 1

Identification of Dry Eye Disease
  Procedures
  Cell Culture, Constructs, and Antibodies Human corneal epithelial (HCE-T) cells were purchased from the RIKEN BioResource Center (Tsukuba-shi, Japan) and used between passages 3 and 15. HCE-T cells were cultured and maintained in DMEM/F-12 containing 4 mg/ml insulin, 100 µg/ml EGF, 500 µg/ml cholera toxin, and 5 µl/ml DMSO. Primary human corneal epithelial cells (PCS-700-010) were purchased from ATCC (Manassas, Va.) and expanded in the suggested medium.

N-terminal deletions of 45, 65, and 71 amino acids and point mutants V69S, I73S, I98S, F104S, L108S, L109S, F112S, I68S/I73S, V91S/L109S, and L108S/L109S/F112S were developed from pLAC. All constructs were confirmed by DNA sequencing. Lacritin and deletion or point mutants, including deletion mutant "C-25", were generated in *Escherichia coli* and purified as described previously (Wang et al, (2006) J. Cell Biol. 174, 689-700)) with additional purification over DEAE in PBS in which lacritin is collected in the flow-through. Purified lacritin was filter-sterilized and stored lyophilized.

Polyclonal N and C terminus-specific anti-lacritin antibodies were respectively generated in New Zealand White rabbits against keyhole limpet hemocyanin-conjugated EDASSDSTGADPAQEAGTS ("Pep Lac N-Term") as "anti-Pep Lac N-term" and against lacritin deletion mutant N-65 as "anti-N-65 Lac C-term" (Bio-Synthesis Inc., Lewisville, Tex.) and characterized. Monoclonal N terminus-specific anti-lacritin antibodies were generated (University of Virginia Lymphocyte Culture Center) in mice against keyhole limpet hemocyanin-conjugated DPAQEAGTSKP-NEEIS and screened through three rounds of cloning against the lacritin deletion mutant C-59 as 1F5-C9-F4 ("1F5"; IgG1).

Tears and Viability Analyses

Tears were collected from 0.5% proparacaine-anesthetized eyes from a total of normal or dry eye individuals by insertion of a filter wicking "Schirmer" strip with millimeter gradations between the lid and eye and individually stored at −70° C. Prior to elution, the total normal or dry eye tear volume was estimated from millimeters of tears drawn into each strip. This defined the final volume of PBS respectively used for elution. Pooled normal or pooled dry eye tears were stored at −70° C. until use.

For FOXO3 translocation assays, HCE-T cells were grown in triplicate to subconfluence (~50%) on coverslips in α-MEM (5.54 mm glucose), sensitized overnight in IFNG (100 units/ml; Roche Applied Science), and treated for 15 min with normal or dry eye tears diluted 1:100 in α-MEM together with TNF (50 ng/ml; PeproTech, Rocky Hill, N.J.) without or with 10 nm lacritin or C-25. Cells were washed, fixed with 4% paraformaldehyde, and immunostained for FOXO3 (1:200; Millipore, Billerica, Mass.) followed by goat anti-rabbit secondary antibody and visualization on a Zeiss LSM 700 microscope.

Some experiments were performed with normal tears that had been immunodepleted of lacritin. For immunodepletion, rabbit anti-Pep Lac N-term and anti-N-65 Lac C-term were jointly immobilized on protein A beads and washed. A rabbit preimmune column was similarly prepared for mock-depleted tears. The flow-through from overnight incubation of each with normal tears was collected and assayed in triplicate on IFNG-sensitized cells with TNF as described above. For validation, the acid eluant from each column was separated by SDS-PAGE, transferred to nitrocellulose, and blotted for lacritin using mouse anti-lacritin antibody 1F5 and a mouse-specific, peroxidase-labeled secondary antibody followed by chemiluminescence detection.

Viability was monitored using the 3-(4,5-dimethyl-2-yl)-2,5-diphenyltetrazolium bromide) (MTT) reduction assay (Invitrogen) or a Nucleocounter (New Brunswick Scientific, Edison, N.J.). Cells were seeded overnight in 24-well plates at a density of 500 cells/mm2 to give rise to ~80% confluence the next day. Then cells were sensitized overnight in IFNG (100 units/ml) in α-MEM and treated in triplicate for 15 min with 10 nm lacritin or lacritin deletion or point mutants or with different lacritin doses in α-MEM together with TNF as described above.

Inclusion of inhibitors was simultaneous with the addition of lacritin or C-25 in all viability and other experiments except where otherwise noted. Inhibitors included PI103 (0.5 μm; EMD, Darmstadt, Germany), rapamycin (10 and 100 nm; EMD), and cyclosporin A (0.1 μm; EMD). One exception was 4-methylumbelliferyl-β-d-xylopyranoside ("xyloside"; 70 and 80 nm; Sigma), which was added during IFNG sensitization and during treatment with TNF and lacritin. The assay was completed by addition of MTT (5 mg/ml) to each well (at 37° C. for 4 h) followed by isopropanol with 0.04 n HCl and measurement at 570 nm using a reference wavelength of 630 nm. Viability was assayed in a Nucleocounter (New Brunswick Scientific).

Results

Tears accumulate on the avascular corneal epithelium, and vascularized conjunctiva, as a translucent film rich in proteins, lipids and metabolites. Beyond its capacity to lubricate the lid, tears are essential for the refraction of light. Equally important and irreplaceable by drugs or drops is the role of tears in promoting corneal epithelial health. When tears are chronically insufficient the epithelium becomes stressed and releases inflammatory cytokines that further exacerbate the situation. Dry eye affects 5-6% of the general population, rising to 6-9.8% and as high as 34%, respectively in postmenopausal women and the elderly. Although the most common eye disease, there is no single gold standard diagnostic test, nor effective treatment. Current approaches include: a) subject questionnaires, b) rose bengal or lissamine green staining of ocular surface damage, c) Schirmer strip measurement of tear volume, d) tear break up time, e) tear evaporation rate, f) tear meniscus height or radius, g) tear film index or turnover rate, h) tear osmolarity, i) lysozyme or lactoferrin assay, and j) tear ferning analysis, each of which have numerous shortcomings.

The tear proteome is estimated to comprise 1,543 proteins, with over half designated as 'intracellular' by Gene Ontology, implying that cell death from normal epithelial renewal may be a contributor. The only growth factor-like molecule downregulated in mild to severe aqueous deficiency was lacritin. Comparison of tears from 73 normals to 129 individuals suffering from aqueous deficient dry eye by 2-D SDS PAGE revealed lacritin to be downregulated in 95% of aqueous deficient dry eye. Lacritin promotes basal tearing when added topically in rabbits. Another tear protein found to be downregulated in dray eye was lipocalin-1. Lipocalin-1 cleanses the ocular surface of lipids that would otherwise interfere with ocular surface wetting. Lacritin was the most severely downregulated protein in contact lens-related dry eye—perhaps in part because it is readily adsorbed on contact lenses. It is also deficient in blepharitis, a common inflammation of the eyelid, associated with evaporative dry eye. However, 2-D SDS PAGE prior to mass spectrometry is necessary to distinguish lacritin downregulation, a method not practical for clinical use.

Several molecules are necessary for lacritin activity. An unusual deglycanated form of syndecan-1 (SDC1) was discovered to be the main cell surface binding protein for lacritin by mass spectrometric sequencing of cell surface proteins bound to lacritin columns at physiological salt. Validation was by affinity precipitation. SDC1 is a widely expressed cell surface heparan sulfate proteoglycan with a carboxy terminal end anchored in the plasma membrane with short cytoplasmic tail, and an ectodomain substituted proximally with chondroitin sulfate chain(s) at serines 184 and 194 (human SDC1; numbering excludes the signal peptide), and distally with up to three heparan sulfate chains (serines 15, 23, 25)—without or with a short chondroitin sulfate chain. Lacritin's C-terminal α-helix binds a domain within SDC1 amino acids 1-50, with binding dependent on prior heparanase deglycanation of heparan sulfate. SiRNA knockdown of SDC1 abrogates lacritin dependent mitogenic activity, as does depletion of heparanase (but not heparanase-2), but can be rescued by addition of exogenous heparanase or with bacterial heparitinase. The binding domain has been narrowed to hydrophobic amino acids 20-30 that enhances lacritin C-terminal α-helicity. Binding was also dependent on substitution of S23 and S25 (and possibly S15) with both heparan sulfate and chondroitin sulfate as a novel hybrid domain of hydrophobic core protein, heparanase cleaved heparan sulfate and adjacent chondroitin sulfate. Heparanase is not widely expressed. N-terminal substitution of SDC1 with chondroitin sulfate is uncommon.

We looked for SDC1 in tears using a highly sensitive chemoluminescent approach. Tears were collected onto Schirmer strips from 146 individuals who were then subjected to vision corrective photorefractive keratectomy or LASIK surgery, with further tear collection 1 day, 1 week, and 1 month later. Tears were stored at −70° C., eluted with a tear equivalent volume of PBS, pooled by time and whether normal (≥15 mm) vs dry eye (≤5 mm) tears, and then separated by SDS-PAGE. Separated tear proteins were transferred to nitrocellulose and blotted with anti-SDC1 mab A-38B. Secondary abs were precleared over a tear column, and ab C-term was precleared over C-59 lacritin truncation mutant. Normal tears were unexpectedly enriched in the rare, heparanase deglycanated form of SDC1 (FIG. 1) targeted by lacritin. Little of the deglycanated form of SDC1 was apparent in dry eye tears. Deglycanated SDC1 can vary in molecular weight from ~90 (FIG. 1) to ~80 kDa or even ~60 kDa—dependent on the level of O-glycosylation that can vary among different epithelia. One day after photorefractive keratectomy or LASIK surgery tear ~90 kDa SDC1 was indistinguishable between normal and dry eye—in keeping with surgery-induced dry eye. A new ~25 kDa SDC1 fragment became apparent in those originally designated as dry eye (FIG. 1). Deglycanated SDC1 and tearing was restored in normal individuals 1 week and 1 month later.

However, the dry eye—associated ~25 kDa band remained (FIG. 1) throughout the assayed timeframe. Thus, ~90 kDa syndecan in tears is a marker of normalcy. Those lacking ~90 kDa syndecan have dry eye. Further, the ~25 kDa form distinguishes dry eye individuals who underwent PRK or LASIK.

Figure 2A:
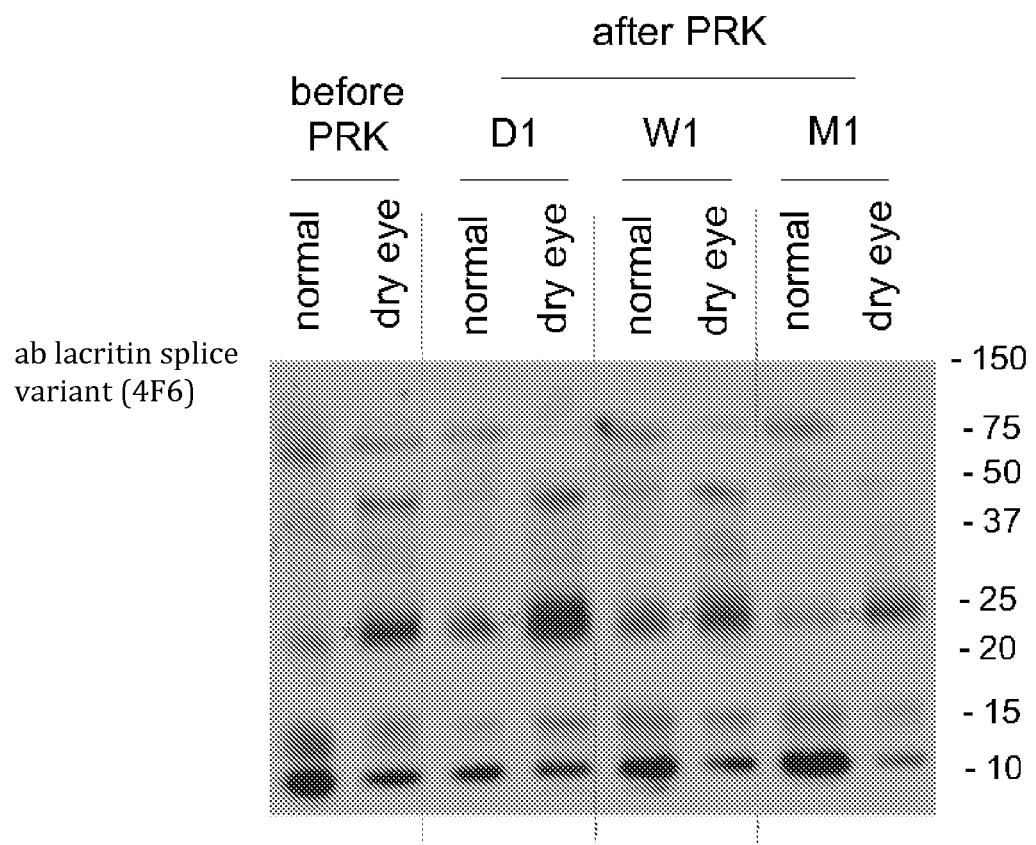
FIGS. 2A & 2B. Detection of elevated levels of inactive lacritin-C splice variant in dry eye tears.
Figure 2B:
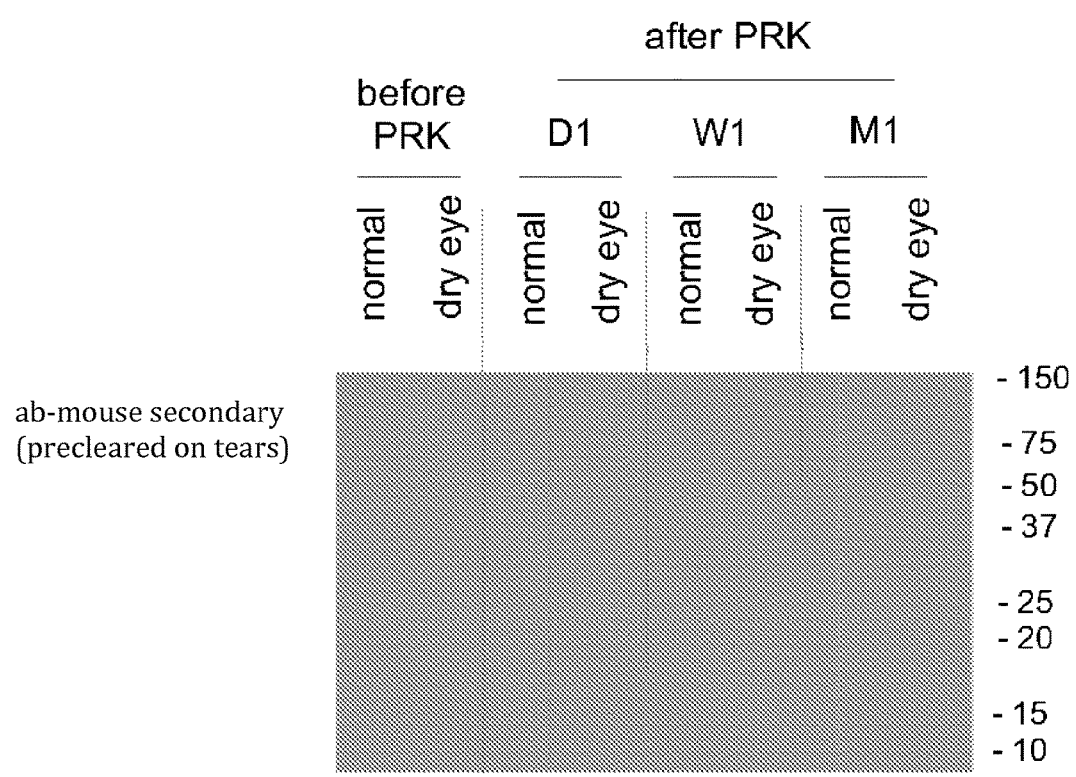
Figures 3A, 3B:
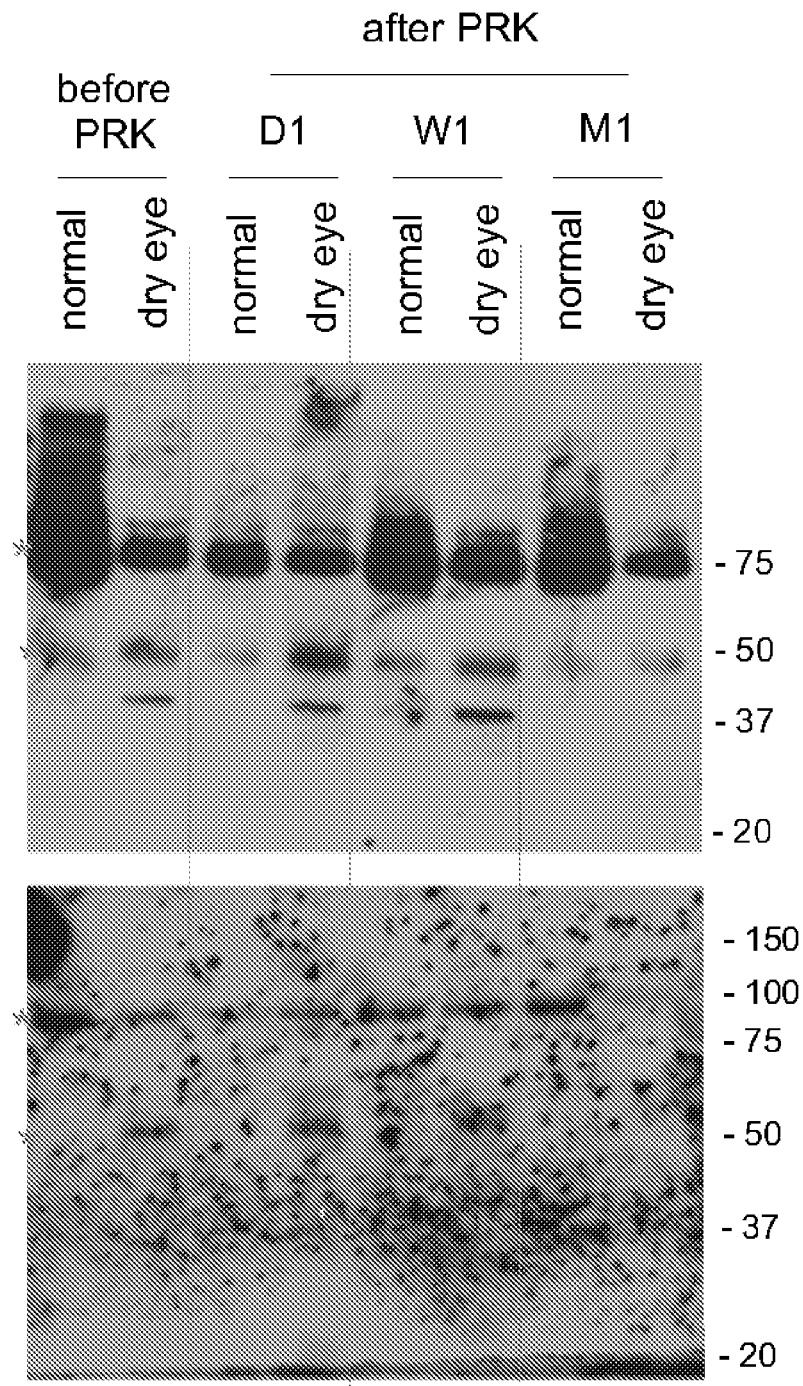
FIGS. 3A & 3B. Detection of more latent heparanase in normal tears vs dry eye tears, and more activated heparanase in dry eye years.

Blotting for the inactive lacritin-c splice variant in tears also proved to be indicative of dry eye (FIG. 2A). Lacritin-c lacks sequence from exons 4 and 5 encoding the C-terminus and has an additional sequence not present in native lacritin. Instead, an inactive novel C-terminus from intron 3 is spliced in. We further discovered differences in tear heparanase with more latent heparanase in normal tears (with the exception of one day after photorefractive keratectomy or LASIK surgery; FIG. 3), whereas active heparanase was abundant in dry eye tears. Secretion of heparanase that has been processed from its latent 65 kDa to active 58 kDa heterodimeric forms is stimulated by UTP. UTP is a proposed treatment for dry eye via a mechanism thought to involve the production of mucins. These observations suggest a potential linkage between lacritin, UTP and heparanase in ocular surface physiology.

Taken together, aqueous deficient dry eye tears are associated with dramatically less deglycanated SDC1 and latent heparanase, but substantially more SDC1 fragment and chronically active heparanase, as well as inactive lacritin-c splice variant at the expense of normal active lacritin. These conditions are appropriate for the exacerbation or initiation of dry eye that can be reversed by topically restoring lacritin.

Identification-Specific Treatment of Dry Eye Disease

Figure 5:
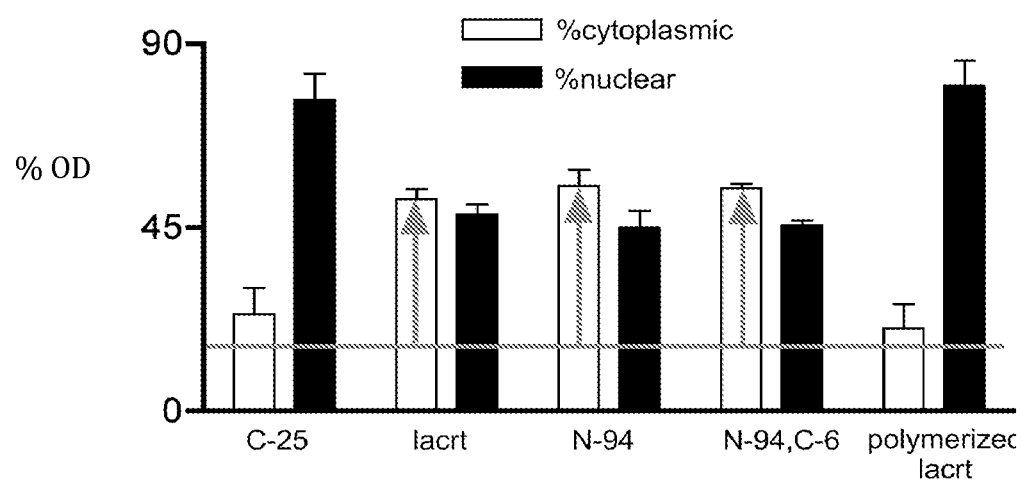
FIG. 5 Comparative pro-survival activity of lacritin and lacritin synthetic peptides. Quantitation of FOXO3 immunostaining in interferon-γ and tumor necrosis factor stressed human HCE-T cells treated with lacritin C-terminal truncation mutant C-25 (negative control; inactive), lacritin (lacrt), lacritin C-terminal peptide N-94 (SEQ ID NO: 7) or N-94/C-6 (SEQ ID NO: 5), or tissue transglutaminase polymerized lacritin (inactive). Dosage for each administered peptide is 10 nM. More nuclear staining indicates stress/death. More cytoplasmic staining (arrows) indicates survival. 203-379 cells were counted for each treatment. Comparison of all but polymerized lacrt vs C-25 by two-way ANOVA with Bonferroni post test, P=0.01.

Commonly used 'artificial tears' temporarily alleviate symptoms associated with dry eye without addressing the cause of those symptoms. An ophthalmic formulation of the anti-inflammatory agent cyclosporine is now in wide use. It and other anti-inflammatory agents are in clinical trials, but generally benefit only ~15% of dry eye subjects. Rather than focusing on inflammatory sequelae, or applying drugs developed for other organ systems, there is benefit in considering the natural biology of the ocular surface and what is missing in dry eye. Downregulation of lacritin monomer, a natural tear protein that promotes basal tearing when added topically to normal rabbit eyes, may be an upstream instigator of dry eye disease. Why is there less lacritin monomer in dry eye? Lacritin monomer is cross-linked into inactive multimers by tissue transglutaminase (TGM2) in tears. This was demonstrated by immunodepleting all lacritin monomer, multimer and fragment from human tears. Recombinant lacritin spiked into immunodepleted tears formed dimers, trimers and tetramers after overnight incubation at 37° C. In the negative control without tears, a small amount of dimer formed. Crosslinking involves glutamine 106 within the lacritin mitogenic domain (amino acids 100-109) that targets syndecan-1. Cross-linked lacritin binds syndecan-1 substantially less and is less active (FIG. 5; right two bars). Blotting suggests that normal human tears contain 0.6 µM TGM2, that thus appears to act as a negative regulator of monomeric lacritin. Human corneal epithelial cells express both TGM1 and TGM2 mRNA's. mRNA expression of both increases with hyperosmolar stress, particularly TGM1, however TGM1 has not been detected in tears. Thus, lacritin may be subjected to enhanced cross-linking and deactivation in dry eye.

To define the lacritin domain necessary for regulation of homeostasis, truncation and point mutants were generated. Inactivity of the C-25 truncation mutant defined a cytoprotective domain in the C-terminus of lacritin that was previously shown to be α-helical and likely amphipathic, and accordingly ordered. The hydrophobic face of amphipathic α-helices can mediate high affinity agonist-receptor or co-receptor interactions. To assay this possibility, hydrophobic residues were singly, doubly, or triply mutated. Also generated were truncations, and the C-terminus ('I3') of the lacritin-c splice variant with completely different sequence from wild type. Amino acid numbering throughout is of mature protein without signal peptide. Hydrophobic face mutants I98S, F104S, L108S/L109S/F112S, and F112S were significantly less active (Wang et al, '13). Activity was unaffected by mutations L65S, I68S/I78S, V69S, and I73S in an adjacent α-helix. Deleting 45, 65 or 71 N-terminal amino acids had no effect, and I3 was inactive. L108, L109 and F112 interact with the syndecan-1 core protein sequence GAGAL.

Basal tears from normal individuals and from those diagnosed with dry eye were incubated with human corneal epithelial cells stressed with the inflammatory cytokines interferon-γ (INFG) and tumor necrosis factor (TNF)—much like their in vivo dry eye counterparts. Nuclear-cytoplasmic translocation of the corneal transcription factor FOXO3 served as a simple readout for cellular stress, with cytoplasmic FOXO3 indicative of restored homeostasis. Nuclear FOXO3 largely transcribes for cell stress or death. In stressed cells treated with normal tears, FOXO3 translocated to the cytoplasm). However with dry eye tears, FOXO3 remained nuclear. Next, lacritin was immunodepleted from normal tears, although normal tears have other growth factors that might compensate. Also dry eye tears were spiked with lacritin. Dry eye tears are both hyperosmolar and inflammatory cytokine-rich. Mock-depleted tears translocated FOXO3 to the cytoplasm, whereas FOXO3 remained nuclear in cells treated with lacritin depleted tears. Dry eye tears spiked with lacritin, but not those spiked with lacritin truncation mutant C-25 (lacking C-terminal 25 amino acids), translocated FOXO3 to the cytoplasm. Lacritin, but not C-25, also translocated FOXO3 in INFG/TNF stressed primary human corneal epithelial cells. Thus, lacritin is the master protector of normal tears.

Figure 4A:
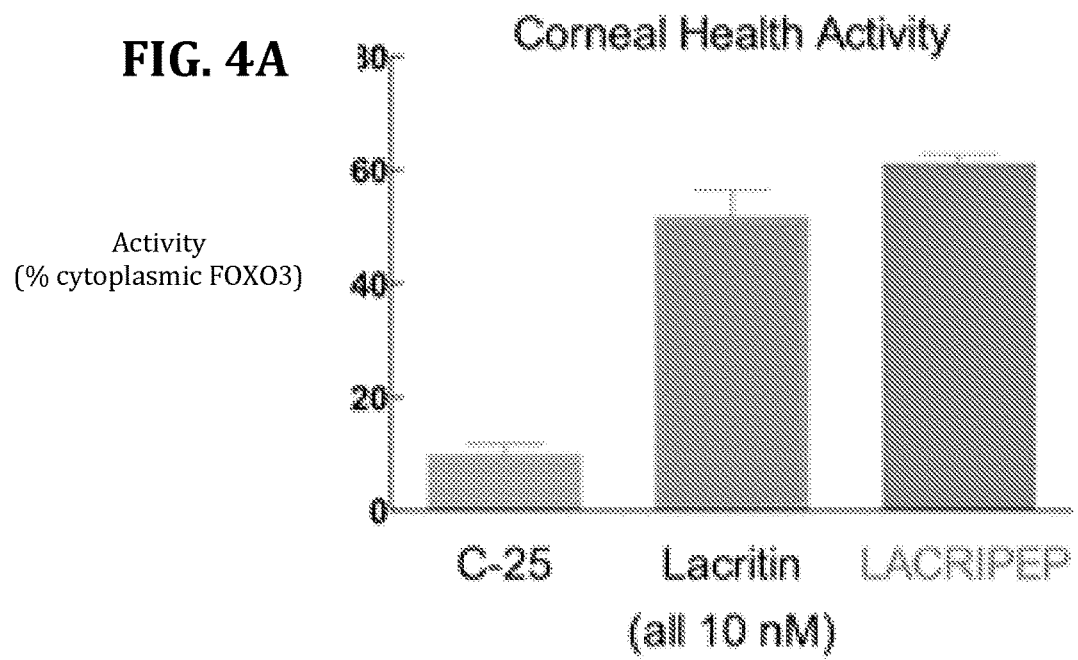
FIGS. 4A-4C: Corneal health restorative activity of lacritin, and a C-terminal 25 amino acid fragment of lacritin (LACRIPEP). Cultured human corneal epithelial cells were treated with inflammatory cytokines to induce stress, and cells were treated with 10 nM of an inactive lacritin truncation mutant (C-25), lacritin or LACRIPEP. Measurements of cytoplasmic staining in a FOXO3 assay (wherein nuclear FOXO3 staining is indicative of cell death) reveal LACRIPEP is equally active as lacritin (See FIG. 4A) in enhancing cell survival relative to the negative control (C-25). Studies in dry eye (Aire-/-) mice also demonstrate the bioactivity of topically administered LACRIPEP. LACRIPEP prevents loss of tearing as dry eye disease develops in Aire(-/-) dry eye mice (FIG. 4B; closed circles) relative to topically administered PBS (opened circles) and Aire(-/-) dry eye mice administered LACRIPEP have less corneal staining, which is an indicator of cell death, as dry eye disease develops (FIG. 4C; closed circles) relative to PBS (opened circles).

This test was repeated using a bioactive C-terminal fragment of lacritin (LACRIPEP; SEQ ID NO: 7). Cultured human corneal epithelial cells were treated with inflammatory cytokines to induce stress as described above, and cells were treated with 10 nM of an inactive lacritin truncation mutant (C-25), lacritin or LACRIPEP. Measurements of cytoplasmic staining in the FOXO3 assay (wherein nuclear FOXO3 staining is indicative of cell death) reveal LACRIPEP is equally active as lacritin (See FIG. 4A) in enhancing cell survival relative to the negative control (C-25). Accordingly, applicants anticipate that LACRIPEP can substitute for lacritin for all applications.

Figure 4B:
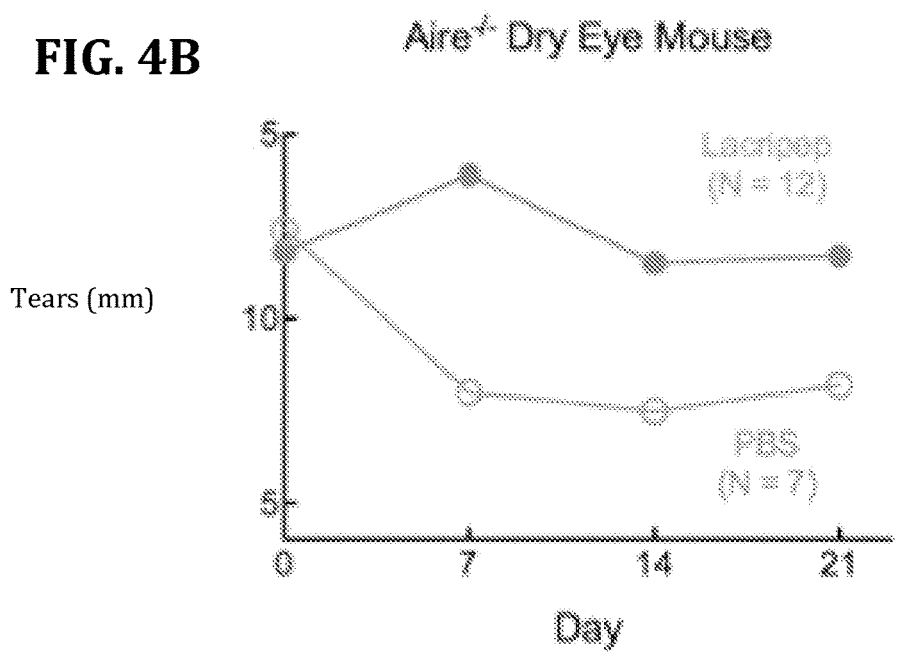

Autoimmune regulator (Aire)-deficient [Aire$^{-/-}$] mice spontaneously develop dry eye without need for dry chambers or scopolamine. Aire$^{-/-}$ mice were dosed three times daily for three weeks with 10 µl of 50 µg/ml lacritin, or in controls with PBS. Several different assays monitored the consequences. A bioactive fragment of lacritin, LACRIPEP (SEQ ID NO: 7), prevents loss of tearing as dry eye disease develops in Aire(−/−) dry eye mice (FIG. 4B; closed circles) relative to topically administered PBS (opened circles), and reduced inflammation of the lacrimal gland. Topical lacritin reduced CD4+T cell infiltration into lacrimal glands measured as the number of lymphocytic foci/per millimeter square area of lacrimal gland tissue (3.68±0.65 per mm·sq lacritin vs. 9.7+1.5 per mm. sq PBS; P=0.01), but had no apparent effect on the pattern or distribution of CD4+T cells into either the corneal stroma (14.6±1.6 lacritin vs 12.4±2.1 PBS) or the limbus (29.6±2.5 lacritin vs 34.6±2.9 PBS.

Figure 4C:
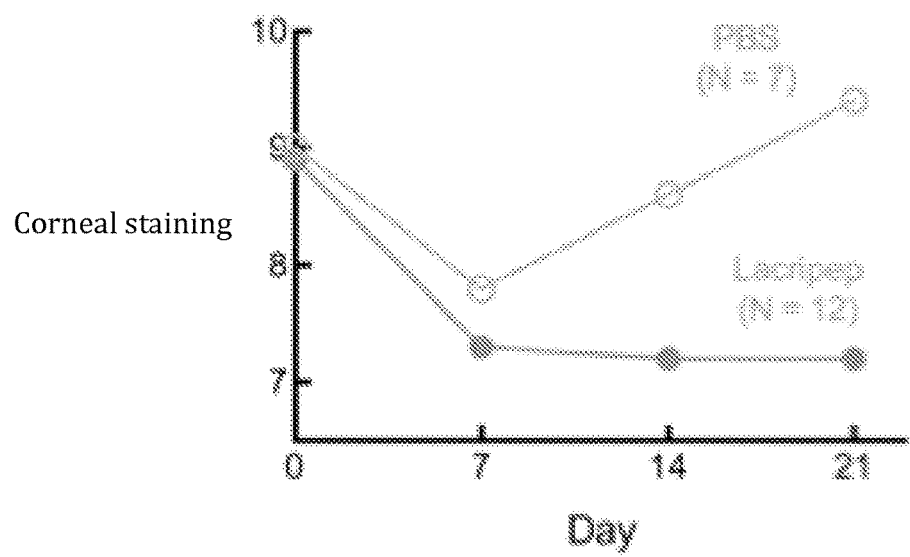

To assess ocular surface mucosal damage from dry eye, eyes of Aire(−/−) dry eye mice were topically administered lissamine green that increasingly stained PBS-treated eyes with time (See FIG. 4C). In contrast, topical lacritin significantly decreased staining (−0.417±0.06 lacritin vs 0.125±0.07 PBS; p=0.02. Further, lacritin diminished levels of keratin 10 (skin epidermal marker), indicating a capacity to block corneal keratinization associated with chronic inflammation, whereas keratin 12) expression (corneal marker) remained stable (80.1±4.8% lacritin vs 85.6±1.8%; P>0.10). In addition, Aire(−/−) dry eye mice administered LACRIPEP were also found to have less corneal staining, which is an indicator of cell death, as dry eye disease develops (FIG. 4C; closed circles) relative to PBS (opened circles). Thus, topical lacritin, and its bioactive fragments thereof, diminished lacrimal gland inflammation and corneal staining in dry eye, and promoted ocular surface differentiation. Importantly, suppression of inflammation and promotion of tearing was achieved without direct contact with inflammatory cells nor with tear producing cells.

Topical lacritin stimulates tearing even without physical access to lacrimal acinar cells. The rapidity of the response is in keeping with corneal sensory nerve activation. Individual corneal sensory nerve activity was monitored at the level of the trigeminal ganglion in rats via previously described methods. Emerging from these studies was the observation that topical lacritin is neural stimulatory. Topical lacritin enhanced the neural 'dry response', and to a lesser extent the neural 'wet response'. The 'dry response' refers to neural activation as a consequence of drying of the cornea, which is thought to be a critical TRPM8-mediated stimulus for tearing, while the 'wet response' occurs when the agonist is present at the corneal nerve terminals. Neither of these responses was affected by negative control truncation mutant C-25, supporting the importance of the C-terminal α-helix in both neural stimulation and tearing. It is likely that the enhanced dry response by lacritin, is due to a modulation of TRPM8 channels: ranging from a fully inhibited TRPM8 state during wet cornea (with lacritin on board) by adrenergic $α_{2A}$ and/or $α_{2c}$ receptors to a completely disinhibited (activated) state during dry cornea (with lacritin removed). Apparent inhibition of the action potentials by lacritin during wet cornea was small because the TRPM8 activity during wet cornea is low to begin with, while it reaches optimal level during dry cornea when dynamic cooling of the ocular surface is taking place. Lacritin may also increase TRPM8 neural density.

Stimulation of the dry response could be by indirect or direct mechanisms. Lacritin stimulation of the corneal epithelium could indirectly target sensory neurons via junctional-like complexes between the two cell types. However, these are thought to be rare. Arguing against a direct mechanism are epithelial tight junctions that would impede lacritin access to nerve endings. However $Ca^{2+}$ and some growth factors can loosen tight junctions. PDGF permeabilizes tight junctions between cultured kidney cells within minutes, as does VEGF of endothelial tight junctions, whereas chronic permeabilization of surface cells of the stratified corneal epithelium is observed in MMP9- or inflammatory cytokine-linked inflammation and in bacterial infection from endotoxin challenge. Lacritin dependent $Ca^{2+}$ mobilization may be sufficient to promote rapid and acute permeabilization for neural access. We expect that a two-step process is involved. First, lacritin or lacritin peptide targeting of superficial corneal epithelial cells promotes subtle loosening of tight junctions, perhaps by transiently increased trafficking of occludin into early endosomes, or by lacritin dependent calcium signaling of the corneal epithelium since calcium regulates tight junction permeability. We expect that the process is activated within 1 min, as per lacritin-stimulated calcium signaling within 20 sec, and lacritin stimulated autophagy by 1 min. In this manner, lacritin or peptide gains entry. Subsequent neural stimulation may be sufficient to trigger reclosure of tight junctions, as per the importance of neural stimulation in corneal wound healing.

Syndecan-1 is a cell surface heparan sulfate proteoglycan that mediates lacritin targeting of cells, but only after heparanase (Ma et al, '06) has exposed GAGAL nestled among heparan sulfate chains. Heparanase also generates heparan sulfate stubs that appear to be required for lacritin binding, suggesting a hybrid GAGAL/heparan sulfate-binding site. To assess the role of this interaction, cells were cultured overnight in 4-methylumbelliferyl-b-D-xylopyranoside ('xyloside') to competitively suppress heparan and chondroitin sulfate assembly. Xyloside completely abrogated lacritin cytoprotective activity. Thus, these activities are dependent on a region in its C-terminus that includes the syndecan-1 binding domain. Further lacritin activities appear to be entirely embodied within the sequences KQFIENGSEFAQKLLKKFS ('N-94/C-6'; SEQ ID NO: 5) (Wang et al., 2006) or KQFIENGSEFAQKLLKKFSLLK-PWA ('N-94'; SEQ ID NO: 7) (Zhang et al., 2013) that when generated synthetically is as potent as lacritin.

Lacritin targeting of corneal sensory neurons. Adrenergic $α_{2c}$ selective antagonist MK912 inhibits lacritin accelerated autophagy in HCE-T cells, as does the syndecan-1 inhibitor xyloside. Both also inhibit lacritin stimulated FOXO3 phosphorylation. Activity profiles of corneal neurons before, during and 1 hr during/after 10 μM lacritin reveal a small inhibition (from ~12 to ~8 spikes/s) follows immediately after the application of lacritin presumably due to $α_2$ adrenergic receptor activation which inhibits TRPM8 channels. Removal of this inhibition after 1 hr of lacritin and washout causes an enhanced excitation of dry (from ~20 to ~23 spikes/s) and wet response (from ~12 to ~16 spikes/s).

Example 2

The monomeric form of tear lacritin is a multifunctional factor responsible for alleviating ocular surface stress. It is also an agonist for basal tearing. Monomeric lacritin targets a heparanase (HPSE) deglycanated form of cell surface syndecan-1 (SDC1). However, polymerized lacritin and the lacritin-C splice variant are both unable to target SDC1 and are therefore inactive. We investigated whether either SDC1 or HPSE might displace monomeric lacritin in dry eye tears, and if SDC1 or HPSE may be inadequate.

Methods:

Tears were collected onto Schirmer strips from 146 individuals before, and 1 day, 1 week and 1 month after photorefractive keratectomy. Tears were stored at −70° C., and later eluted with a tear equivalent volume of PBS, and pooled by time and normal (≥15 mm) vs dry eye (≤5 mm) tears. Tears were separated by SDS-PAGE and blotted with anti-N-terminal specific lacritin mab 1F5, anti-C-terminal specific lacritin ab 'ab C-term', anti-lacritin-C splice variant mab 4G6, anti-SDC1 mab A-38B, and with anti-heparanase abs #733 and #1453. Secondary abs were precleared over a tear column, and ab C-term was precleared over C-59 lacritin truncation mutant.

Results:

Ab C-term detected less lacritin monomer in dry eye vs normal tears, a deficiency apparently compensated in dry eye by enhanced lacritin-C splice variant. The 1F5 mab epitope is shared by both forms, and thus the presumed hybrid band appeared greater in dry eye. Normal tears were enriched in latent (uncleaved) HPSE and deglycanated SDC1. One day after PRK, lacritin-C was further increased in dry eye, and both SDC1 and HPSE less in normals. Return to pre-PRK conditions was apparent by 1 month.

Conclusions:

Aqueous deficient dry eye tears are associated with decreased lacritin monomer, increased lacritin-C splice variant, and less deglycanated SDC1 and latent HPSE. These conditions are appropriate for the exacerbation or initiation of dry eye.

Example 3

Stability of the 25 Amino Acid C-Terminal Fragment of Lacritin

Figure 6A:
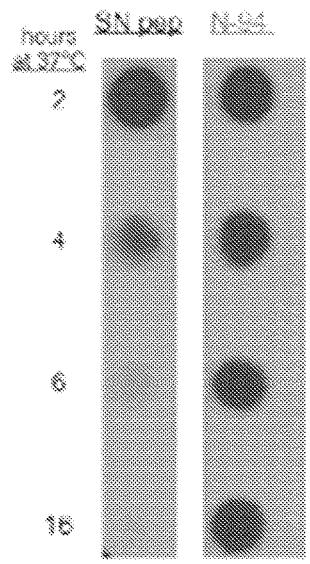
FIGS. 6A & 6B LACRIPEP shows surprising stability in human tears.
Figure 6B:
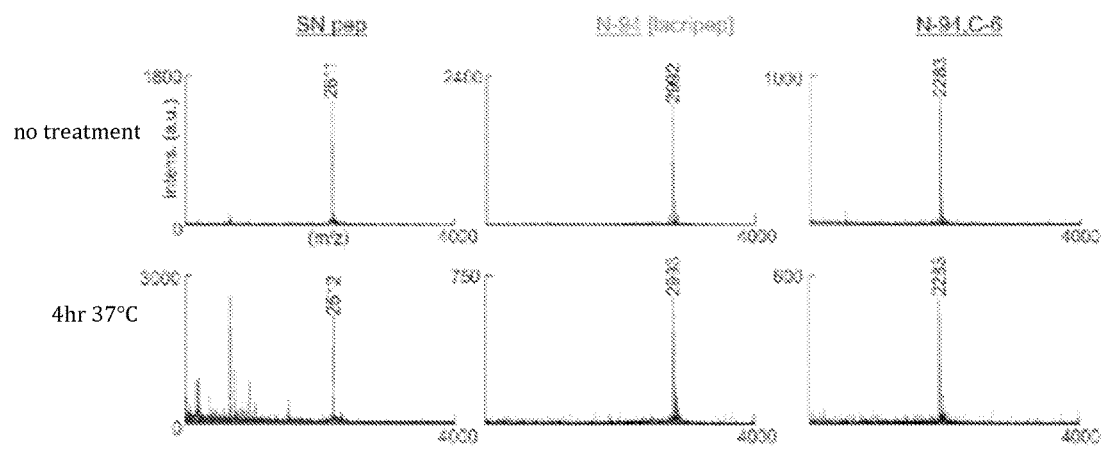

A limitation of most synthetic peptide drugs is their protease sensitivity. Only HIV protease retropepsin and cathepsin K appear capable of cleaving LACRIPEP according to PROSPER (Protease specificity prediction server) analysis, with the former cutting in the middle and the latter removing the last alanine. Retropepsin would inactivate LACRIPEP, while cathepsin K would have no effect. However neither protease is found in normal human tears. Nonetheless, tears are rich in other proteases. We therefore incubated LACRIPEP in normal human tears at 37° C. for 2, 4, 6 and 16 hr. For immunoblotting, we first removed all endogenous lacritin by immunodepletion. Remarkably, LACRIPEP was stable for at least 16 hr as indicated in FIG. 6A, representing immunoblots of a protease sensitive positive control 'SN pep' from a different protein and LACRIPEP ('N-94') after incubation in lacritin-depleted human tears for 2-16 hr at 37° C. Mass spectrometric analysis of the SN pep, Lacripep ('N-94'), and Lacripep without six C-terminal amino acids ('N-94/C-6') demonstrated the relative stability of the three peptides after incubation in lacritin depleted tears for 4 hr at 37° C. (FIG. 6B). Surprisingly, the smaller C-terminal fragment of lacritin (N-94/C-6; SEQ ID NO: 5) was found to be not as stable as the LACRIPEP peptide (SEQ ID NO: 7). Although mass spec analysis suggests that Lacripep ('N-94'), and Lacripep without six C-terminal amino acids ('N-94/C-6') have similar stability in tears, and Lacripep without six C-terminal amino acids ('N-94/C-6') was stable in phosphate buffered saline for 29 days at 62° C. (FIG. 6B), immunoblotting reveals that N-94/C-6 loses epitopes after incubation in lacritin depleted tears for 4 hr at 37° C. whereas Lacripep ('N-94') does not. Accordingly, the final 6 amino acids of native lacritin have relevance in enhancing the stability of bioactive fragments of lacritin making N-94 a superior pharmaceutical peptide relative to N-94/C-6.

Figure 7A:
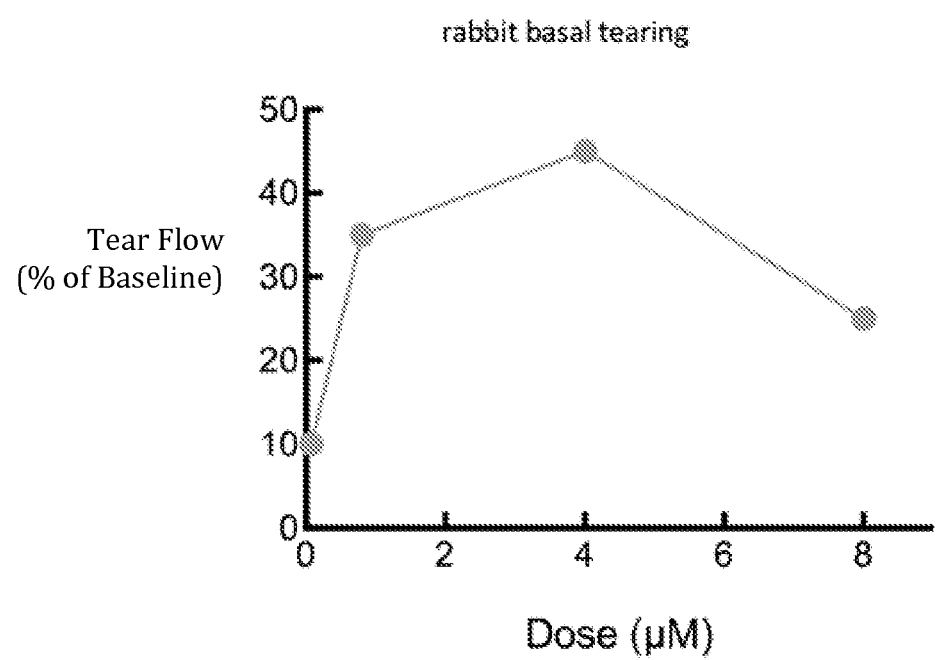
FIGS. 7A & 7B Biphasic dose response of LACRIPEP. Biphasic dose response of topical LACRIPEP was demonstrated testing rabbit basal tearing (FIG. 7A) and in rat corneal sensory nerve stimulation (pLAC.
Figure 7B:
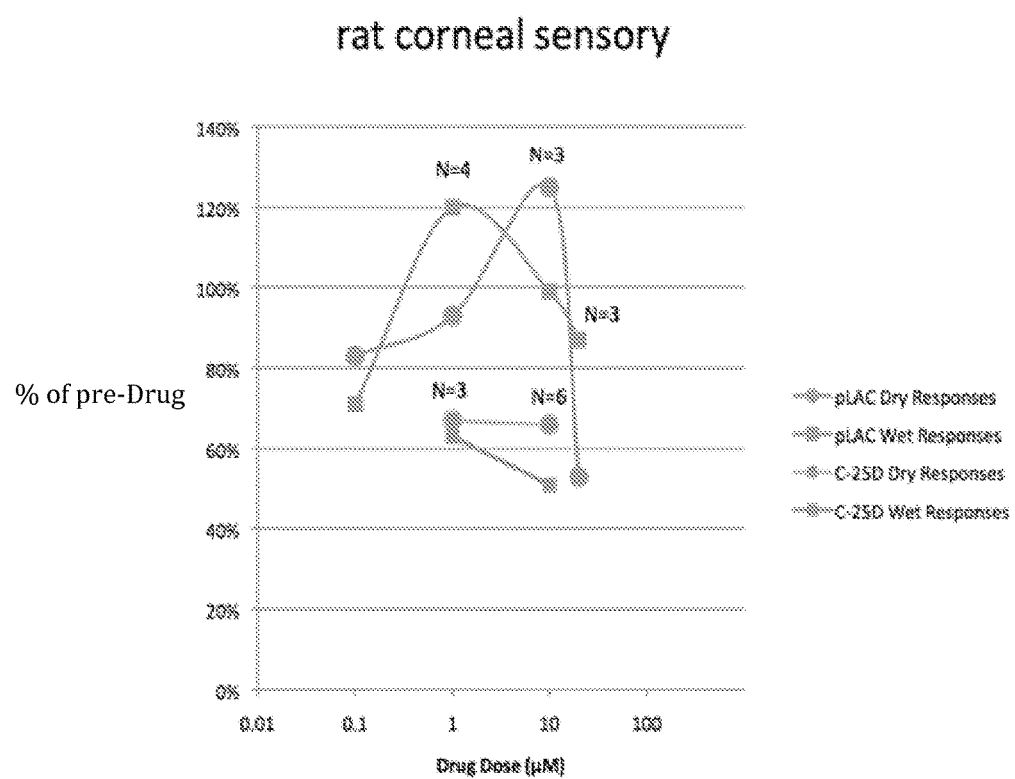

Another advantage of LACRIPEP is its low dose optimum. In human cell culture its optimal dose is 1-10 nM. In animal studies, ~4 µM (0.0012%) is optimum (FIGS. 7A & 7B). 4 µM LACRIPEP has also been found to be bactericidal, but not hemolytic. Lacritin as a whole protein does not have bactericidal activity.

Figure 8:
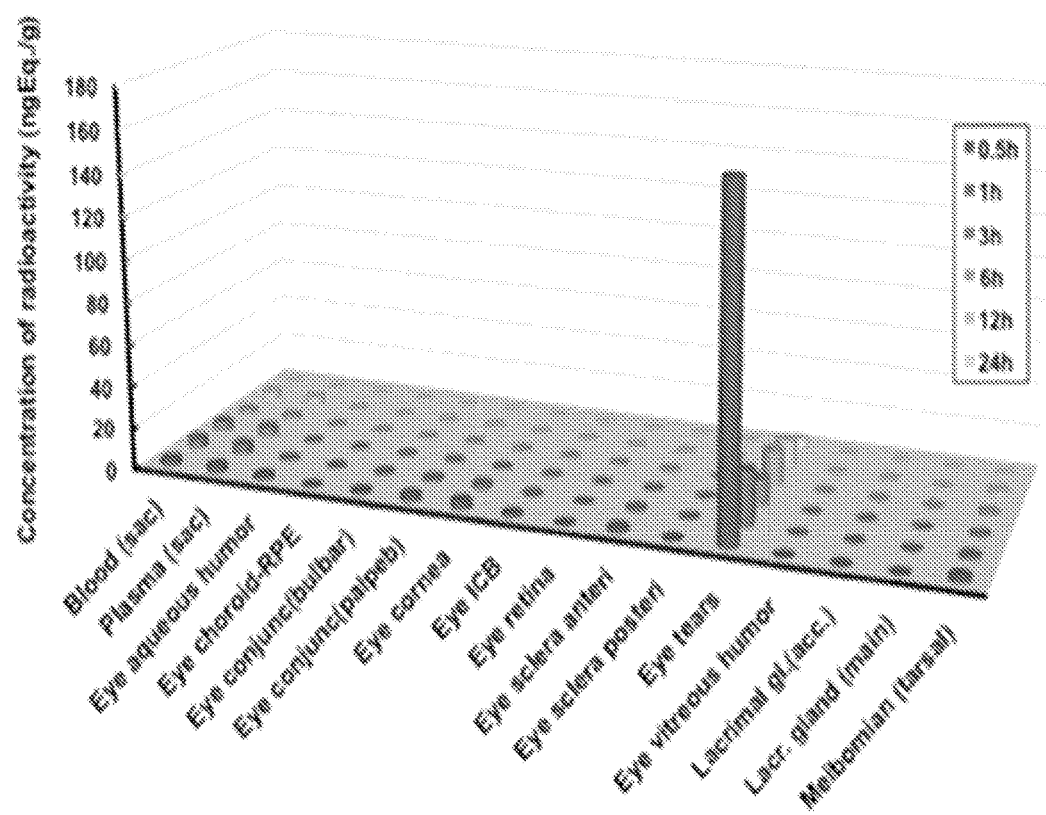
FIG. 8 Distribution of a single 4 μM dose of topical $^{125}$I-Lacripep-Y on rat eyes. Slight amounts of $^{125}$I-Lacripep-Y are detectable in blood and plasma. A considerable amount is retained in tears.

To monitor LACRIPEP in whole body toxicity studies, LACRIPEP was synthesized with a single C-terminal tyrosine for iodination to form $^{125}$I-Lacripep-Y. Rats administered a single 4 µM dose of $^{125}$I-Lacripep-Y demonstrated high retention in eye tears with minimal levels detected in the blood and serum (see FIG. 8).

Example 4

A Cleavage-Potentiated Fragment of Tear Lacritin is Bactericidal

Experimental Procedures

Tears and Tear Immunodepletion—Normal human basal tears were collected. Briefly, tears from 0.5% proparacaine anesthetized eyes were collected onto preweighed wicks and flash-frozen for "70° C. storage. Tears were eluted by immersion of each strip in 30 #1 of PBS for 20 min, followed by centrifugation. For immunodepletion, 10-fold diluted tears were incubated overnight (4° C.) or for 1 h at room temperature with protein A beads (0.2 ml, NAb Spin Kit, Peirce/Thermo Scientific) saturated with "anti-N-65 Lac C-term" or preimmune Ig. N-65 is a lacritin truncation mutant lacking 65 N-terminal amino acids. The tear flow-through after centrifugation (5000 # g for 1 min) was then assayed for antibacterial activity.

Lacritin Constructs, Purification, Synthetic Peptides, and Mass Spectrometry—Lacritin N-terminal truncations N-55, N-65, N-71, and N-75 were generated by PCR from parent cDNA pLAC, as described previously (Zhang et al, (2013) J. Biol. Chem. 288, 12090-12101). N-terminal deletions of 80 (N-80) and 86 (N-86) amino acids were generated using forward primers GGTGGTCATATGAAAGCAG-GAAAAGGAATGCACGG (SEQ ID NO: 9) and GGTG-GTCATATGCACGGAGGCGTGCCAGGTGG (SEQ ID NO: 10) 3$, respectively, and common reverse primer GGTGGTCATATGTATATCTCCTTCTTAAAG (SEQ ID NO: 11). All constructs were verified by sequencing. Bacterial protein expression and purification of recombinant lacritin and lacritin truncations were performed as described previously (Zhang et al, (2013) J. Biol. Chem. 288, 12090-12101). Briefly, cleared cell (ER2566 or BL21-CP) lysates were loaded on chitin columns (IMPACT-CN System; New England Biolabs Inc., Beverly, Mass.) equilibrated with 50 mM Tris, 0.5 M NaCl (pH 8), followed by 20 column volumes of washing, elution with 50 mM 2-mercaptoethanol for 16 h at room temperature in the same buffer, extensive dialysis against PBS (4° C.), and protein quantitation. Further DEAE purification removed a ~9-kDa lacritin proteolytic fragment and bacterial contaminants in which lacritin was collected as the flow through with 140 mM NaCl in phosphate buffer, pH 7.2. Synthetic peptides N-80/C-25, N-94, N-94/C-6, N-94/C-10, N-94/C-15, N-99, and N-104 were synthesized by Genscript (Piscataway, N.J.) with acetylated Ntermini. Purity was 95%. C-termini of all were amidated, with the exception of lacritin C-terminal N-94, N-99, and N-104. N-64/C-31 was neither amidated nor acetylated and was synthesized by the University of Virginia Biomolecular Research Facility. The nature of the lacritin ~9-kDa fragment was pursued by Western blotting. Briefly, lacritin before and after DEAE separation was separated by SDS-PAGE and then transferred and blotted with anti-Pep Lac N-terminal and anti-N-65 Lac C-terminal antibodies, respectively diluted 1:200 or 1:400 in PBS containing 0.3% Tween 20. Detection was with ECL.

For fragment purification, chitin-enriched lacritin was dialyzed against phosphate buffer containing 14 mM NaCl (pH 7.2). Following incubation with DEAE equilibrated in the same buffer, the ~9-kDa fragment was collected in the flow-through, whereas intact (18 kDa) lacritin was eluted with 140 mM NaCl in phosphate buffer, pH 7.2. After determination of protein concentration (BCA assay), both were aliquoted, lyophilized, and stored at −70° C. Analysis was by SDS-PAGE on 4-20% gradient gels. The identity of the ~9-kDa fragment was determined by mass spectrometry.

Bacterial Growth, SYTOX Green Assays, and on Column Cleavage—*E. coli* (ATCC (Manassas Va.) catalog no. 10536), *S. epidermidis* (ATCC catalog no. 12228), and *P. aeruginosa* (ATCC catalog no. 9027) were grown to mid-log phase in 50 ml of Luria-Bertani (LB) medium and washed three times in phosphate buffer containing 10 mM NaCl (pH 7.2; PB—NaCl) with centrifugation. Pellets were resuspended in 1 ml of PB—NaCl.

For lacritin inhibition assays, 50 ul of bacterial pellets each diluted 1:100 in PB—NaCl were incubated for 1.5 h (37° C.) with 100 ul of lacritin, lacritin truncations, or synthetic peptides at a final concentration of 0.1-6 uM. Mixtures were diluted 1:10 in PB—NaCl before plating 100 ul in quadruplicate on LB agar plates for overnight growth at 37° C. Colonies were manually counted. In other experiments, mid-log *E. coli* was treated at 37° C. for 0, 1, 2, or 3 h with 2 uM lacritin or lacritin truncations or with ampicillin (5 uM) or tetracycline (2 uM). After each treatment, 100 ul was centrifuged, resuspended in 1 ml of PB—NaCl, and plated (100 ul) onto LB agar for overnight growth (37° C.) and colony counting.

For salt sensitivity studies, pelleted and washed mid-log phase *E. coli*, *S. epidermidis*, or *P. aeruginosa* were resuspended in 1 ml of PB—NaCl and then treated as above with PB—NaCl or with 3 uM N-65 in 130, 280, or 380 mosmol/liter PB—NaCl for 1.5 h (37° C.). Mixtures were diluted 1:10 in PB—NaCl before plating 100 ul of each in quadruplicate on LB agar plates for overnight growth at 37° C. Colonies were manually counted.

For bacterial permeability assays, pelleted and washed midlog phase *E. coli* were resuspended in 1 ml of PB—NaCl and then treated as above with 3 uM lacritin, N-65, or C-25 or with 10% Triton X-100. Similarly, washed mid-log phase *S. epidermidis* were resuspended in 1 ml of PB—NaCl and then treated with lacritin or C-25 or a ~9-kDa purified lacritin fragment. Later, 1 ul of 0.5 mM SYTOX Green was added to each well of 96-well fluorescent microtiter plates. Readings were taken at 5-min intervals at respective excitation and emission wavelengths of 485 and 538 nm using a Fluoroskan Ascent FL fluorometer (Thermo Fisher Scientific). In parallel, SYTOX Green internalization was visualized by confocal microscopy after 1 h of 10% Triton X-100, PB—NaCl, or 3 uM N-65 treatment of washed mid-log phase *E. coli*.

For cell-free synthesis without glycosylation, full-length lacritin cDNA in pLacSL was PCR-amplified and subcloned into pTXB1 supplied by the manufacturer (New England Biolabs, Ipswich, Mass.). Cell-free synthesis and subsequent removal of ribosomes, followed by metal affinity resin adsorption of His-tagged factors, was performed as per the manufacturer's instructions (New England Biolabs; PURExpress). Immediately following expression, an aliquot was stored at −60° C. Other aliquots were incubated at 37° C. for 24 and 48 h. Each was separated by SDS-PAGE, transferred, and blotted with anti-N-65 Lac C-terminal antibodies.

For lacritin cleavage assays, supernatants from saturated 50-ml overnight cultures of *S. epidermidis* were collected by centrifugation (10 min; 11,000 rpm). Each supernatant was then incubated for 4, 16, and 20 h (37° C.) in PB—NaCl with chitin beads containing lacritin-intein immobilized via N-termini. C-terminal cleavage products were collected by PBNaCl washing, separated by SDS-PAGE, transferred, and blotted with anti-N-65 Lac C-terminal antibodies. In some experiments, supernatants and lysates from overnight cultures of *S. epidermidis, Staphylococcus aureus, P. aeruginosa*, and *E. coli* were incubated overnight (37° C.) with lacritin in solution in PB—NaCl. Mixtures were then separated by SDS-PAGE, transferred, and blotted with anti-N-65 Lac C-terminal antibodies. Parallel studies monitored the integrity of chitin-intein-immobilized lacritin in PB—NaCl at 37° C. for 0, 24, 48, and 72 h or for 24 h (37° C.) with 1 uM pepstatin, 10 uM bestatin, 100 uM antipain, 1 mM 4-benzenesulfonyl fluoride hydrochloride, 100 uM chymostatin, 10 uM E64, 100 uM leupeptin, or 10 mM phosphoramidon or for 24 h after boiling for 5 min at 100° C.

Hemolysis Assay—The method of Cerovsky et al. was followed with some modifications. Washed sheep red blood cell pellets (MP Biomedicals, Santa Ana, Calif.) were suspended for 1 h at 37° C. in 565 ul of PBS plus 100 ul of lacritin, N-55, N-65, N-71, N-75, N-80, or C-25 at a final concentration of 2 uM or with N-65, N-64/C-31, N-80/C-25, N-94, N-94/C-6, N-94/C-10, N-94/C-15, N-99, or N-104 at a final concentration of 6 uM. As respective positive and negative controls, Triton X-100 (final concentration of 5%) or PBS was included in place of lacritin or lacritin fragments. After centrifugation (250×g; 5 min), the absorbances of supernatants at 540 nm were monitored.

Metabolome Analysis—Washed mid-log *E. coli* were incubated with 6 uM N-65 or PB—NaCl for 15 min at 37° C. in replicates of six, each at $1 \times 10^8$ cells/replicate. Cells were then washed once, and pellets were flash-frozen for storage at −70° C. Unbiased metabolite analysis was performed by Metabolon Inc. (Durham, N.C.) using GC/MS and LC/MS/MS. 78 metabolites were identified.

Statistical Analyses—With the exception of the single metabolomic analysis, all experiments were performed at least three times. Statistical analysis of metabolite data was performed, where raw data values were first log transformed to be closely distributed as a normal distribution and then assessed by a non-parametric Wilcoxon test and two-sample t test. For both tests with p & 0.05, metabolites were considered significantly different and further analyzed by hierarchical clustering for their association patterns. Data are reported as the mean+/−S.E.

Results

Lacritin Bactericidal Activity in Tears—Tears protect the surface of the eye against environmental pathogens and are enriched in the prosecretory mitogen lacritin, which flows onto the eye during basal and reflex tearing. Lacritin is 21% identical to dermcidin, whose proteolytically processed C terminus contributes to the bactericidal activity of human sweat. We sought to determine whether lacritin or a lacritin fragment(s) have bactericidal activity. Half-diluted basal tears completely blocked *E. coli* growth and *E. coli* is a significant contributor to bacterial conjunctivitis in the developing world, as is *P. aeruginosa*. We tested tears that had been passed over immobilized anti-N-65 Lac C-terminal antibodies (ab C-term) to immunodeplete both lacritin and C-terminal lacritin fragments, or over preimmune Ig (mock-depleted). Both were diluted 10-fold for dose-dependent challenge of *E. coli* and *P. aeruginosa*. Mock-depleted tears suppressed *E. coli* and *P. aeruginosa* colonies in a tear volume-dependent manner. This contrasted with C-terminal antibody-immunodepleted tears, which were as ineffective as the phosphate buffer negative control.

Lacritin's C Terminus Contains a Bactericidal Domain—Lacritin's C terminus contains three predicted α-helices each validated by circular dichroism. The most C-terminal α-helix is amphipathic and targets syndecan-1 as an initiator of corneal epithelial cell proliferation and survival, largely via hydrophobic face residues. Association of amphipathic α-helices with bacterial membranes can be destabilizing. To explore whether these or other lacritin domains are bactericidal, we generated recombinant lacritin and lacritin truncations. Each was generated as an intein fusion protein, purified on chitin to also remove the intein tag and then on DEAE to exclude bacterial contaminants. Lacritin and truncations were then assayed in equimolar (2 uM) amounts in the presence of mid-log *E. coli*, *P. aeruginosa*, or *S. epidermidis*. *P. aeruginosa* is an eye pathogen often responsible for keratitis in contact lens wear. *S. epidermidis* is a common cause of conjunctivitis and keratitis and is abundant in blepharitis, an eyelid inflammation associated with slightly altered tear composition, including selectively less lacritin. Lacritin without truncation had no effect on the appearance of colonies, with numbers equivalent to the phosphate buffer negative control. However, few colonies were apparent with lacritin lacking 65 (N-65) or 80 (N-80) amino acids from the N-terminus, an effect completely or partly negated by removing six additional amino acids (N-86) in *E. coli* or *P. aeruginosa* but not *S. epidermidis*. Amino acids 81-86 comprise the sequence LAKAGKG (SEQ ID NO: 12), which aligns with a sequence in a potent dermcidin fragment SSL-25 with an amino acid identity of 44%.

To determine whether the LAKAGKG (SEQ ID NO: 12) region was responsible, we generated AKAGKGMHG-GVPGG (SEQ ID NO: 13; amino acids 81-94; N-80/C-25), comprising the truncation-narrowed portion of the SSL-25 homologous region. Also generated were partially overlapping LKSIVEKSILLTEQALAKAGKGMH (SEQ ID NO: 14; amino acids 65-88; N-64/C-31) and C-terminal KQFIENGSEFAQKLLKKFSLLKPWA (SEQ ID NO: 7; amino acids 95-119; N-94). Unexpectedly, colonies were abundant with N-80/C-25 and N-64/C-31, whereas few or no colonies were apparent with N-94, a region only 12.5% identical with the C-terminus of dermcidin. To narrow this site, we generated synthetic peptides with amino acids sequentially removed from the carboxy terminus N-94/C-6, N-94/C-10, N-94/C-15 and N-99 ENGSEFAQKLLKKF-SLLKPWA (SEQ ID NO: 15), and N-104 (FAQKLLKKF-SLLKPWA (SEQ ID NO: 16). N-94 and N-104 were fully active but not the other peptides, although N-94/C-6 (SEQ ID NO: 5) was slightly so. N-65 is bactericidal and equipotent to ampicillin. In dose response studies, N-104 was almost as effective as N-65, with a half-maximal inhibition of about 1 uM for *E. coli* and about 1-1.5 uM for *P. aeruginosa*, a dose range common to antimicrobial peptides.

Discussion

The rationale for exploring whether lacritin might be bactericidal was its 21% identity with dermcidin, whose proteolytically processed C terminus contributes to the bactericidal activity of human sweat and is in tears. Surprisingly, dermcidin primary sequence homology was not the source of lacritin activity. Only 40.7% identity is shared between dermcidin's bactericidal SSL-25 peptide and the homologous lacritin region that as a synthetic peptide was inactive. Instead, lacritin N-104 fragment with 7% dermcidin identity embodies the core activity, a hybrid domain consisting of an N-terminal amphipathic α-helix and hydrophobic C-terminal coiled coil tail, together appropriate for bacterial membrane contact and insertion, as was apparent by rapid entry of membrane-impermeable SYTOX Green in N-65-treated cells. Surprisingly, a C-terminal 25 amino acid fragment KQFIENGSEFAQKLLKKFSLLKPWA (SEQ ID NO: 7; amino acids 95-119; N-94) was found to be fully active, wherein removal of 6 terminal amino acids (e.g. KQFIENGSEFAQKLLKKFS; SEQ ID NO: 5) substantially reduced the bactericidal activity of the peptide.

Example 5

Although topical application of ophthalmic products has remained the most popular and well-tolerated administration route for patient compliance, the bioavailability of eye drops is severely hindered by blinking, baseline and reflex lacrimation, and nasolacrimal drainage. One solution to enhance the therapeutic index of topical treatments is through the application of polymeric nanoparticles as drug carriers.

One solution to enhance the therapeutic index of topical treatments is through the application of polymeric nanoparticles as drug carriers. Polymeric nanoparticles displaying therapeutic ligands at the corona can interact with complex biomolecular architectures through multiple simultaneous interactions (multivalency) and exhibit the well-defined sizes required for efficient tissue penetration. One such material capable of being employed as the scaffold are thermo-responsive elastin-like polypeptides (ELPs). ELPs are composed of the repetitive pentapeptide motif (Val-Pro-Gly-Xaa-Gly)n (SEQ ID NO: 24) and exhibit unique reversible inverse phase transition temperatures, Tt, below which they solubilize and above which they phase separate. Tt can be modulated through guest residue (Xaa) selection and changes in the number of pentameric repeats, n.

Inspired by the motivation to further explore lacritin's function on the ocular surface, enhance its bioavailability, and better target the corneal epithelium, we utilized a diblock ELP (SI) nanoparticle scaffold to bioengineer LSI nanoparticles with multivalent presentation of lacritin at the surface.

Materials and Methods

Materials and Equipment

TB DRY® Powder Growth Media was purchased from MO BIO Laboratories, Inc. (Carlsbad, Calif.). NHS-rhodamine was purchased from Thermo Fisher Scientific (Rockford, Ill.). SV40-Adeno vector transformed cornea cells (RCB 2280, HCE-T) were purchased from Riken Cell Bank, Japan. Keratinocyte-SFM medium supplied with Bovine Pituitary Extract (BPE) and prequalified human recombinant Epidermal Growth Factor 1-53 (EGF) was purchased from Gibco Invitrogen (Life Technologies, NY). Calcium Indicator Fluo-4, AM, cell permeant was purchased from Life Technologies (NY). Algerbrush II with a 0.5 mm burr was purchased from The Alger Company, Inc., TX. In vivo studies were conducted using in house bred 12 week female non-obese diabetic (NOD) (Taconic Farms, Germantown/NY, USA) mice.

Construction of LSI Nanoparticles

Genes encoding for ELPs (SI) were synthesized by recursive directional ligation in pET25b(+) vector. A sequence encoding human lacritin without secretion signal peptide was designed using the best *E. coli* codons in EditSeq (DNAStar Lasergene, WI). A thrombin cleavage site was designed between the lacritin sequence and ELP tag via insertion at the BseRI site. Lacritin gene flanked by NdeI and BamHI restriction digestion sites at the 5' and 3' ends was purchased in the pIDTSmart-KAN vector from Integrated DNA Technologies (IDT) as follows:

```
                                              (SEQ ID NO: 25)
CATATGGAAGACGCTTCTTCTGACTCTACCGGTGCTGACC

CGGCTCAGGAAGCTGGTACCTCTAAACCGAACGAAGAAATCTC

TGGTCCGGCTGAACCGGCTTCTCCGCCGGAAACCACCACCACC
```

```
GCTCAGGAAACCTCTGCTGCTGCTGTTCAGGGTACCGCTAAAG

TTACCTCTTCTCGTCAGGAACTGAACCCGCTGAAATCTATCGTT

GAAAAATCTATCCTGCTGACCGAACAGGCTCTGGCTAAAGCTG

GTAAAGGTATGCACGGTGGTGTTCCGGGTGGTAAACAGTTCAT

CGAAAACGGTTCTGAATTCGCTCAGAAACTGCTGAAAAATTCT

CTCTGCTGAAACCGTGGGCTGGTCTGGTTCCGCGTGGTTCTG

GTTACTGATCTCCTCGGATCC.
```

The above gene was subcloned into the pET25b(+) vector and the LSI gene was synthesized by ligation of ELP SI gene via the BseRI restriction site. Correct cloning of the fusion protein gene was confirmed by DNA sequencing. LSI fusion proteins were expressed in BLR (DE3) *E. coli* (Novagen Inc., Milwaukee, Wis.) for 24 h in an orbital shaker at 37° C. at 250 rpm and purified via inverse phase transition cycling.

Characterization of LSI Phase Behavior and Nanoparticle Formation

The phase diagram for LSI fusion protein was characterized by optical density change at 350 nm as a function of solution temperature using a DU800 UV-Vis Spectrophotometer (Beckman Coulter, Brea, Calif.). Tt was defined at the point of the maximum first derivative. Self-assembly of nanoparticles was measured using dynamic light scattering (DLS) using a DynaPro-LSR Plate Reader (Wyatt Technology, Santa Barbara, Calif.). Light scattering data were collected at regular temperature intervals (1° C.) as solutions were heated from 5 to 50° C. The results were analyzed using a Rayleigh sphere model and fitted into a cumulant algorithm based on the sum-of-squares value. The critical micelle temperature (CMT) was defined as the lowest temperature at which the Rh is significantly greater than the average monomer Rh.

TEM Imaging of LSI Nanoparticles

The TEM imaging was carried out on a FEI Tecnai 12 TWIN microscope (Hillsboro, Oreg.) at 100 kV. Briefly, a 100 uM solution (5 uL) was initially deposited on a copper grid with carbon film (CF400-Cu, Election Microscopy Sciences, Hatfield, Pa.). After removing the excess amount of solution with filter paper, the samples were negatively stained with 2% uranyl acetate, followed by removing excess uranyl acetate after 30 s. The samples were then dried under room temperature for at least 3 h before use in imaging.

SV40-Immortalized Human Corneal Epithelial Cell (HCET) Culture

SV40-immortalized HCE-T cells (Riken Cell Bank, Japan) were grown in keratinocyte-SFM media (KSFM, Life Technologies, Rockville, Md.) containing bovine pituitary extract (BPE, 50 mg/ml) and epidermal growth factor (EGF, 5 ng/ml). Cell passages 4-6 were used for Ca2+ imaging, scratch and uptake assays in 35 mm coverslip-bottomed dishes. To optimize responsiveness upon stimuli, cells were starved with EGF and BPE free medium for 24 h before experimentation.

Ca2+ Imaging

HCE-Ts were rinsed twice with Ca2+ and Mg2+ free phosphate buffer saline (PBS) and incubated at 37° C. for 20 min fresh KSFM medium containing 2.5 mM calcium probe Fluo-4AM (Invitrogen Life technologies, NY). The cells were then rinsed twice with NaCl Ringer buffer (145 mM NaCl, 5 mM KCl, 1 mM CaCl$_2$, 1 mM KH2PO4, 1 mM MgCl$_2$, 10 mM glucose, and 10 mM HEPES, osmolarity 300, pH 7.4) and kept in the same buffer at room temperature for 30 m. For Ca2+ free medium, 1 mM Ca2+ was replaced with 0.5 mM EGTA. The cells were illuminated at 488 nm, and their emission was monitored every 3.15 s at 510 nm using Zeiss LSM 510 Meta confocal microscope system. The field of interest contained 24 to 45 cells, and the fluorescent intensity change was calculated for each region with image-analysis software. Ca2+ dynamics were evaluated using the changes in fluorescence intensity of Fluo-4AM. The data are presented as percentage change in fluorescence intensity at each time point (Ft) to the first time point (F0) reading: (Ft–F0)/F0×100%.

In Vitro Scratch Closure Assay

For a scratch assay, confluent HCE-T monolayers were scraped in a straight line to create a scratch wound with a p200 pipet tip. Cells were rinsed with KSFM medium without BPE or EGF to remove debris and then incubated with fresh KSFM medium containing BPE (50 mg/ml) and EGF (5 ng/ml), LSI, or medium without growth factors (No treat). Phase contrast images of the wound at the beginning and after 24 h treatment were captured using Zeiss LSM 510 Meta confocal microscope system.

Exogenous Cell Uptake Assay

SI and LSI nanoparticles were conjugated with NHS-rhodamine (Thermo Fisher Scientific Inc, Rockford, Ill.) via covalent modification of the amino terminus. Conjugation was performed in 100 mM borate buffer (pH 8.0) for 2 h (LSI) or overnight (SI) at 4° C. followed by desalting on a PD10 column (GE Healthcare, Piscataway, N.J.) to remove free dye. Briefly, after the cells were rinsed with fresh medium without BPE and EGF, 10 mM rhodamine labeled proteins were added into the dish. After incubation at 37° C. for different time points, the cells were rinsed and images were acquired using Zeiss LSM 510 Meta confocal microscope system.

Murine Corneal Abrasion and Recovery Study

Briefly, 12 week female NOD mice were anesthetized with an i.p. injection of xylaxine/ketamine (60-70 mg+5 mg/kg) and placed on a heating pad. After cleaning the ocular surface with eye wash (OCuSOFT, Inc., TX), the corneal epithelium of the right eye was removed down to the basement membrane using an algerbrush II (The Alger Company, Inc., TX); the left eye was left intact as a contra lateral control. Mice were allowed to heal for 24 h with 2 doses (5 ml) of KSFM medium containing BPE (50 mg/ml) and EGF (5 ng/ml), 100 mM LSI, 100 mM SI, or no treatment at 12 h intervals. After staining the ocular surface with 5 ml 0.6 mg/ml fluorescein (Akorn, Ill.), images of the abrasion wound were captured using a Moticam 2300 camera after 12 h and 24 h.

Statistics

All experiments were replicated at least three times. Maximum fluorescence intensity change in Ca2+-mediated fluorescence was analyzed using a non-paired t-test. Scratch wound healing quantification was analyzed using a one-way ANOVA followed by Tukey's post hoc test. HCE-T uptake was analyzed using two-way ANOVA followed by Bonferroni post-test and murine corneal epithelium recovery from abrasion wound were analyzed using Kruskal-Wallis non-parametric ANOVA. Corneal wound healing comparison between LSI and LS96 after 12 h treatment was analyzed using Mann-Whitney U test. A p value less than 0.05 was considered statistically significant.

Results and Discussion

The ELP lacritin fusion called LSI forms thermoresponsive nanoparticles

Two derivatives of lacritin were formed, each comprising an ELP tag:

LSI
(SEQ ID NO: 26)
GEDASSDSTGADPAQEAGTSKPNEEISGPAEPASPPETTTTAQETSAAAV

QGTAKVTSSRQELNPLKSIVEKSILLTEQALAKAGKGMHGGVPGGKQFIE

NGSEFAQKLLKKFSLLKPWAGLVPRGSG(VPGSG)$_{48}$(VPGIG)$_{48}$Y;
and

LS96
(SEQ ID NO: 27)
GEDASSDSTGADPAQEAGTSKPNEEISGPAEPASPPETTTTAQETSAAAV

QGTAKVTSSRQELNPLKSIVEKSILLTEQALAKAGKGMHGGVPGGKQFIE

NGSEFAQKLLKKFSLLKPWAGLVPRGSG(VPGSG)$_{96}$Y.

LSI and LS96 were cloned into a pET25(+) vector, expressed in E. coli, and purified using inverse phase transition cycling. LSI was expected to undergo thermally-mediated assembly similar to SI and form nanoparticles above its phase transition temperature (Tt), while LS96, with lacritin gene fused to the soluble macromolecule S96, was developed as a control that does not phase separate until significantly above physiological temperatures. After confirming the purity and molecular weight of expressed proteins, their phase diagrams were characterized using optical density as a function of temperature. While monomeric ELPs undergo a single phase transition from solubility to coacervate, certain ELP diblock copolymers display two steps of assembly in response to heating: (i) soluble monomers assemble into stable nanoparticles above Tt1; and (ii) at a higher temperature, Tt2, the nanoparticles themselves coacervate. For ELPs such as LSI, Tt1 is thus defined as the critical micelle temperature (CMT) above which nanoparticles are favorable (32.3° C. at 25 mM). Tt2, or the bulk phase transition temperature, represents the temperature at which these nanoparticles further assemble into coacervates. In striking contrast to its SI scaffold, LSI only shows one phase transition at 18.4° C. (25 mM). Moreover, LSI illustrated less concentration dependent phase transition compared to the SI scaffold, as demonstrated by a decreased slope when Tt was fit by the equation: Tt=m log [$C_{ELP}$]+b, where $C_{ELP}$ is the concentration, m is the slope, and b is the transition temperature at 1 mM. Eqn (1) permits the estimation of Tt over a broad range of concentrations, which may be encountered in vivo. In our recent reports, suppression of the ELP concentration dependence correlates with assembly mediated by the fusion domain itself, which we have reported in fusion between a single chain antibody and also a disintegrin. Based on the unexpected observation that LSI exhibits a single phase transition, dynamic light scattering (DLS) was used to determine whether particles form above or below this Tt.

Both constructs were thus compared by DLS to monitor the temperature dependent assembly process. Surprisingly, LSI preassembled into 30-40 nm nanoparticles even below Tt. Above Tt, it began to favor larger nanoparticles ranging from 130-140 nm. SI remained as 20-30 nm micelles at physiologically relevant temperatures. In combination with the optical density data, this suggests that lacritin itself mediates partial assembly of small aggregates that proceed to assemble larger structures above the Tt1 mediated by SI.

To further examine the dominant structures formed by LSI and SI, we observed their morphologies when dried from room temperature using transmission electron microscopy (TEM). Consistent with DLS, while SI formed a mono-dispersed micelle structure with an average diameter of 36.5+/−5.8 nm and LSI formed larger nanoparticles that exhibit average diameters of 67.1+/−11.5 nm. Regardless, both SI and LSI appear capable of forming nanostructures.

LSI nanoparticles exhibit mitogenic activity using SV-40 transduced human corneal epithelial cells.

Upon injury, one of the earliest reactions of many epithelial cells is a transient Ca2+ wave spreading across the monolayer cell sheet. The Ca2+ wave triggers downstream signaling pathways responsible for cell migration, proliferation and other events associated with wound repair. Lacritin has been reported as stimulating Ca2+ wave propagation throughout HCE-Ts and further studies have confirmed that this Ca2+ signal is associated with lacritin's protection of HCE cells stressed with benzalkonium chloride and maintenance of cultured corneal epithelia homeostasis. To confirm whether LSI maintains mitogenic activity of lacritin, we tested both calcium transients and scratch wound healing assays based on the reported HCE-T model. We first tested intracellular Ca2+ wave propagation in HCE-T cells loaded with Fluo-4 AM under either LSI or SI treatment. The fields of interest containing 24 to 45 cells were chosen and the fluorescent intensity change of ten individual cells was calculated using LSM 510 image-analysis software. Percentage change in fluorescence intensity at each time point (Ft) to the first time point (F0) reading: (Ft−F0)/F0×100% was used to quantify Ca2+ signal. The signal triggered by SI was negligible, evoking only a 0.054+/−0.049 fold maximum fluorescence intensity change compared to baseline. The addition of LSI nanoparticles, however, resulted in a significantly rapid calcium influx into the cells with a maximum fluorescence intensity 4.399+/−1.043 fold of F0 ($p<0.0001$). Moreover, HCE-T cells appeared to have 'memory' for exogenous LSI treatment, as treating the same group of cells for the second time with the same concentration resulted in a broader peak for Ca2+ influx, which extended peak duration from 40 to 70 s. Downstream of Ca2+ mediated signaling, HCE-Ts are known to initiate more rapid motility and proliferation, which can be visualized during the closure of a scratch made on a confluent sheet of cells.

To visualize the in vitro effect of LSI, we applied a scratch to a sheet of cells and captured the timelapse healing process. Each treatment was performed in triplicate and four independent wound distances in each well were measured for analysis. After 24 h of treatment, a very low concentration of LSI (10 nM) significantly accelerated scratch wound healing compared to plain medium without growth factors (***$p<0.001$). This effect was comparable to a positive control containing BPE and EGF.

LSI Nanoparticles Undergo Uptake into HCE-Ts

Encouraged by LSI's in vitro mitogenic activity, we further explored whether exogenous LSI can enter the HCE-Ts. The cells were thus incubated with NHS-rhodamine labeled LSI and SI nanoparticles for different time points. Consistent with lacritin-mediated uptake, LSI underwent cell uptake into HCE-Ts in a time dependent manner. Significant cell entry was observed 10 m following incubation, and after 1 h, LSI nanoparticles accumulated within the peri-nuclear region. Upon quantification, LSI exhibited significantly higher cytosolic fluorescence than SI nanoparticles ($p<0.0001$). Nanomaterials of different sizes, shapes, and charges have been widely used in biomedical imaging, tissue targeting, and cell uptake. More recently, the use of nanoparticles to crosslink membrane receptors more efficiently to regulate downstream signaling has attracted enormous attention, especially in antibody mediated receptor crosslinking.

LSI Nanoparticles Heal a Corneal Abrasion on Non-Obese Diabetic (NOD) Mice

We proceeded to investigate LSI nanoparticles in vivo efficacy via topical eye drops. In this study, we developed a corneal epithelial abrasion model on female NOD mice to assess the wound-healing effect of LSI nanoparticles. Non-obese diabetic (NOD) mice are frequently used as an animal model for impaired wound healing in humans. Reduced cell proliferation, retarded onset of the myofibroblast phenotype, reduced procollagen I mRNA expression, and aberrant control of apoptotic cell death were observed in NOD group. The NOD mouse model was selected for evaluation of the in vivo activity of LSI nanoparticles. Briefly, a circular abrasion wound with a diameter of around 2 mm was created on the right eye of the animal with an algerbrush II without damaging the limbal region. Immediately after imaging, 5 ml of 100 mMLSI nanoparticles, SI nanoparticles, or control EGF+BPE were topically administered to the ocular surface, and this treatment was repeated once 12 h after wound initiation. Images of the wound were captured at time 0, 12 h, and 24 h using fluorescein staining under cobalt blue light. The initial wound healing comparison study included 4 mice under each treatment group, with the left eye intact as a contralateral control. After experimentation, wound-healing images were analyzed using ImageJ. Mean fluorescein intensity, wound area, total fluorescein (total=mean fluorescein intensity×wound area), fluorescein percentage of initial value, wound area percentage of initial value (PctArea), and total fluorescein percentage of initial value were determined by a blind reviewer and compared between groups at 12 h and 24 h using Kruskal-Wallis non-parametric testing. No significant inflammation or any other adverse effects were observed upon treatments. Notably, LSI at both 12 and 24 hours significantly decreased the percentage of initial wound area (PctArea) compared to SI (p=0.001), EGF+BPE (p=0.001), and no treatment groups (p=0.001), suggesting that LSI is the best formulation to accelerate recovery of the corneal epithelium. To corroborate the fluorescein imaging result, we further processed the corneal epithelium after 24 h for histology analysis. Briefly, corneas were fixed, sectioned across the defect, and stained by hematoxylin and eosin.

Pathology of Corneal Epithelium (EP);

Bowman's membrane (BM); stroma (ST); Descenet's membrane (DM); endothelium (EN) was evaluated. Remarkably, the corneal epithelium of the LSI treatment group showed complete recovery with a smooth, reconstituted surface, absent of inflammation. While the fluorescein test revealed partial resistance to staining at 24 h in the SI group, the regenerated corneal epithelium did not complete differentiation. Having demonstrated that the mitogenic lacritin protein remains active when decorated on a protein polymer nanoparticle, we next investigated whether ELP-mediated particle assembly is required to achieve this result. To address the significance of ELP assembly in vivo, the efficacy of LSI nanoparticles can be directly compared with a thermally nonresponsive lacritin fusion protein called LS96. Both LSI and LS96 contain the lacritin sequence followed by an ELP containing 96 total pentameric repeats; however, the ELP S96 does not phase separate until above physiological temperatures. Optical density measurements, in fact, revealed that LS96 does not display any observable phase transitions in phosphate buffered saline. In addition, DLS confirmed that LSI has a much larger hydrodynamic radius than LS96 at 37° C.

Using these two related formulations of lacritin ELPs, the corneal defect study in NOD mice was both to confirm the ability of LSI to close the epithelium after 12 h and compare this closure with that of LS96. To better evaluate our experimental observation, we further increased the sample size to eight mice per group, with all right eyes receiving the abrasion procedure. Interestingly, LSI healed the abrasion wound significantly (p<0.05) faster than the non thermoresponsive LS96 fusion. This finding directly supports the contention that ELP-mediated assembly is involved with the enhancement of LSI.

CONCLUSIONS

To accelerate the corneal wound healing process, a multivalent ELP nanoparticle was used as a means of delivering a candidate biopharmaceutical, the mitogen lacritin, to the ocular surface. This lacritin ELP fusion, LSI, displays thermoresponsive self-assembly properties similar to the unmodified SI nanoparticle and presents accessible lacritin at its corona at physiologically relevant temperatures. LSI nanoparticles trigger calcium dependent cell signaling, internalize into cells, and facilitate scratch closure in monolayers of a human corneal epithelial cell line (HCE-Ts). When topically applied on the ocular surface of NOD mice following removal of the corneal epithelium, LSI nanoparticles promoted faster wound healing compared to SI and untreated groups. Most importantly, the LSI nanoparticles produce faster regeneration of the corneal epithelium compared to a control lacritin ELP fusion, called LS96, that does not undergo thermally-mediated assembly. Overall, this study highlights the potential of ELPs as nanoparticle scaffolds to effectively deliver protein therapeutics to the ocular surface and repair abrasion wounds.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

What is claimed is:

1. A method comprising determining the concentration of 90 kDa deglycanated syndecan-1 (SDC-1) in a tear sample and determining if a decreased level of 90 kDa deglycanated SDC-1 is present in the sample relative to a predetermined standard, and/or detecting the presence of 25 kDa SDC-1 in a tear sample.

2. The method of claim 1, comprising determining the concentration of 90 kDa deglycanated SDC-1 in a tear sample and determining if a decreased level of 90 kDa deglycanated SDC-1 is present in the sample relative to a predetermined standard.

3. The method of claim 1, comprising detecting the presence of 25 kDa SDC-1 in the tear sample.

4. The method of claim 1, comprising determining the concentration of 90 kDa deglycanated SDC-1 in a tear sample and determining if a decreased level of 90 kDa deglycanated SDC-1 is present in the sample relative to a predetermined standard, and detecting the presence of 25 kDa SDC-1 in a tear sample obtained from a single subject.

5. The method of claim 1, further comprising screening the tear sample for the presence of inactive lacritin-C splice variant and/or latent heparanase.

6. The method of claim 1, comprising detecting the presence of 25 kDa SDC-1 and inactive lacritin-C splice variant in the tear sample.

7. The method of claim 1, further comprising contacting an ocular surface of a subject from which the tear sample was collected with a pharmaceutical composition comprising a lacritin polypeptide if a decreased level of 90 kDa deglycanated SDC-1 is present in the sample relative to a predetermined standard and/or the presence of 25 kDa SDC-1 is detected in the sample.

8. The method of claim 7, wherein the lacritin polypeptide is a polypeptide of SEQ ID NO: 1 or a bioactive fragment of lacritin selected from the group consisting of
KQFIENGSEFAQKLLKKFS (SEQ ID NO: 5);
KQFIENGSEFAQKLLKKFSLLKPWA (SEQ ID NO: 7);
KQFIENGSEFANKLLKKFS (SEQ ID NO: 6);
KQFIENGSEFANKLLKKFSLLKPWA (SEQ ID NO: 8) and
a derivative of SEQ ID NO: 5, SEQ ID NO: 6, SEQ ID NO: 7 or SEQ ID NO: 8 that differs from SEQ ID NO: 5, SEQ ID NO: 6, SEQ ID NO: 7 or SEQ ID NO: 8 by one, two or three amino acid substitutions, additions or deletions.

* * * * *